US006214334B1

(12) United States Patent
Lee et al.

(10) Patent No.: US 6,214,334 B1
(45) Date of Patent: *Apr. 10, 2001

(54) COMPOSITIONS AND METHODS FOR PRODUCING AND USING HOMOGENOUS NEURONAL CELL TRANSPLANTS TO TREAT NEURODEGENERATIVE DISORDERS AND BRAIN AND SPINAL CORD INJURIES

(75) Inventors: Virginia M. -Y. Lee; John Q. Trojanowski, both of Philadelphia, PA (US)

(73) Assignee: Trustees of the University of Pennsylvania, Philadelphia, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/303,973

(22) Filed: May 3, 1999

Related U.S. Application Data

(63) Continuation-in-part of application No. 09/122,019, filed on Jul. 24, 1998, which is a continuation of application No. 08/640,894, filed on Jun. 7, 1996, now Pat. No. 5,792,900, which is a continuation of application No. 08/150,368, filed on Nov. 9, 1993, now abandoned, which is a continuation-in-part of application No. 07/911,980, filed on Jul. 10, 1992, now abandoned, which is a division of application No. 07/780,715, filed on Oct. 21, 1991, now Pat. No. 5,175,103.

(51) Int. Cl.[7] .................................................. A61K 48/00
(52) U.S. Cl. ........................ 424/93.1; 424/93.7; 435/325; 435/347; 435/353
(58) Field of Search ................................ 424/93.1, 93.2, 424/93.7; 435/325, 347, 353

(56) References Cited

U.S. PATENT DOCUMENTS 5,082,670 * 1/1992 Gage et al. ........................... 424/520
5,175,103 * 12/1992 Lee et al. ........................... 435/172.3
5,792,900 * 8/1998 Lee et al. ................................. 800/2

OTHER PUBLICATIONS

Spencer DD et al. New Eng J Med 327:1549–1555, 1992.*
Hansson E. Brain Res 366:159–168, 1986 (abstract).*
Vernadakis, A Int Rev Neurobiol 30:149–224, 1988 (abstract).*
Autillo–Touati et al J Neurosci Res 19:326–42, 1988 (abstract).*
Zigmond et al. Life Sciences 35: 5–18, 1984.*
Brinton RD et al. Neurochem Res 22:1339–1345, 1997.*
Freed CR et al. The New England J of Med. 327:1541–1548. 1992.*

* cited by examiner

Primary Examiner—Scott D. Priebe
Assistant Examiner—Ram Shukla
(74) Attorney, Agent, or Firm—Law Office of Jane Massey Licata

(57) ABSTRACT

Methods of treating individuals suspected of suffering from diseases, conditions or disorders of the Central Nervous System which comprise implanting stable, homogeneous post-mitotic human neurons into the individual's brain are disclosed. Methods of treating individuals suspected of suffering from injuries, diseases, conditions or disorders characterized by nerve damage which comprise implanting stable, homogeneous post-mitotic human neurons at or near a site of said nerve damage are also disclosed.

6 Claims, 6 Drawing Sheets

COMPOSITIONS AND METHODS FOR PRODUCING AND USING HOMOGENOUS NEURONAL CELL TRANSPLANTS TO TREAT NEURODEGENERATIVE DISORDERS AND BRAIN AND SPINAL CORD INJURIES

This application is a continuation-in-part of U.S. patent application Ser. No. 09/122,019, filed Jul. 24, 1998, which is a continuation of U.S. application Ser. No. 08/640,894, filed Jun. 7, 1996, now U.S. Pat. No. 5,792,900, which is a continuation of U.S. application Ser. No. 08/150,368, filed Nov. 9, 1993, abandoned, which is a continuation-in-part of U.S. application Ser. No. 07/911,980, filed Jul. 10, 1992, abandoned, which is a divisional of U.S. application Ser. No. 07/780,715, filed Oct. 21, 1991, now U.S. Pat. No. 5,175,103.

This invention was supported in part by funds from the U.S. government (NS Grant No. 18616) and the U.S. government may therefore have certain rights in the invention.

FIELD OF THE INVENTION

The present invention relates to compositions useful for and methods of transplanting stable, homogeneous populations of neuron cells into non-human animals in order to generate non-human animal models useful to study human diseases, conditions and disorders. The present invention relates to compositions useful for and methods of transplanting stable, homogeneous populations of neuron cells into individuals in order to treat or prevent diseases, conditions and disorders, especially those characterized by loss, damage or dysfunction of the brain and/or loss, damage or dysfunction of an individuals neurons at other sites in the individual's body including the spinal cord.

BACKGROUND OF THE INVENTION

The transplantation of major categories of central nervous system (CNS) cells (i.e. neurons, astrocytes) or CNS tissue fragments offers opportunities to study the developmental biology and immunological properties of these cells, to create animal models of CNS diseases and injuries and to develop alternative strategies for the treatment of spinal cord injuries and progressive neurodegenerative disorders such as Alzheimer's disease, Parkinson's disease, Huntington's disease, amyotrophic lateral sclerosis and hereditary ataxia as well as to study other diseases, conditions and disorders characterized by loss, damage or dysfunction of neurons including transplantation of neuron cells into individuals to treat individuals suspected of suffering from such diseases, conditions and disorders. Indeed, recent pioneering efforts to utilize human fetal mesencephalic tissue grafts to ameliorate the extrapyramidal manifestations of drug induced and idiopathic Parkinson's disease emphasize the potential of transplanted human CNS tissues for the treatment of human neurodegenerative diseases (Freed, C. A., et al. 1992 *New Engl. J. Med.* 327:1549–1555; Spencer, D. D. et al. 1992 *New Engl. J. Med.* 327:1541–1548; and Widner, H., et al. 1992 *New Engl. J. Med.* 327:1556–1563). However, the results of these efforts have not been completely satisfactory.

The immortalization of CNS progenitor cells using constructs containing temperature sensitive promoters has enabled transplantation of genetically engineered precursors of neurons and glia, but brain grafts of these progenitors have given rise to mixed populations of glial and neuronal progeny (Cattaneo, E., and R. McKay 1991 *TINS* 14:338–340; Renfranz, P. J., et al. 1991 *Cell* 66:713–729; Snyder, E. Y., et al. 1992 *Cell* 68:33–51). An alternative strategy has been to use neuron-like transformed cell lines obtained from tumors of the CNS, but neoplastic neuron-like cells usually cannot be induced to permanently exit the cell cycle or they develop into tumors when transplanted into the rodent brain (Fung, K.-F. et al. 1992 *J. Histochem. Cytochem.* 40:1319–1328; Trojanowski, J. Q., et al. 1992 *Molec. Chem. Neuropathol.* 17:121–135; and Wiestler, O. D. et al. 1992 *Brain Pathol.* 2:47–59). A slowly dividing human neuronal cell line obtained from a child with unilateral megalencephaly was shown to exhibit a neuron-like phenotype in culture but grafts of these cells in the rodent CNS showed a mixture of neuronal and mesenchymal phenotypic properties (Poltorak, M., et al. 1992 *Cell Transplant* I:3–15).

Thus, regeneration of injured spinal cord or brain tissue has been an elusive goal for many years. Over 250,000 Americans are spinal cord injured, with 15,000 new injuries reported each year. More than half of them were injured between the ages of 16 and 30, with the majority (90%) of people surviving and living near normal life spans. So far, medicine has improved the quality of care and life for those with spinal cord injuries. However, modern care is expensive, in some cases reaching $1.35 million per person and as much as $4 million per institutionalized patient.

The cells of the spinal cord form a complex circuit which underlies the transmission of sensory information centrally and motor commands peripherally. The complex processing required for the execution of such intricate behaviors is reflected in the complexity of the types of neurons in the spinal cord. The many morphological subtypes of neurons collectively express most known neurotransmitters, neuromodulators and receptors, such as serotonin (5-HT), noradrenaline, glycine, acetylcholine, GABA and glutamate. Often many transmitters and modulators are present within the same cell. For example, serotonergic fiber neurons have been shown to co-express thyrotropin releasing hormone (TRH), 5-HT and substance P in the same terminals (Shapiro, S., 1997, *Neurosurgery*, 40, 168–177). Replacement of the phenotypic variation normally present in the spinal cord is therefore a central goal of therapeutic research.

Numerous therapies have been tried over the years. For example, U.S. Pat. No. 4,966,144 discloses a method of transplanting a nerve graft into a transected site of the spinal cord and irradiating the site with low energy light. The nerve graft is a peripheral nerve segment or spinal cord segment and is placed in the injured area so that its longitudinal axis is parallel to that of the spinal cord.

U.S. Pat. No. 5,639,618 discloses a stable line of lineage-specific neuronal stem cells. The stem cells are constructed from blastocyst-derived ES cells transfected with a reporter construct under the control of the Otx regulatory region, Otx being an early marker for neurogenesis. The reporter construct is used to segregate the neuronal stem cells by FACS isolation or other methods. The segregated cells are then plated and permitted to terminally differentiate.

U.S. Pat. No. 5,618,531 discloses a method for increasing the viability of cells which are administered to the brain or spinal cord. The method is accomplished by attaching the cells to a support matrix and implanting the support matrix into the brain.

U.S. Pat. No. 5,135,956 discloses using long-chain (23 to 29 carbons) fatty alcohols and prodrug esters to cause extension of neurites in vivo and facilitate healing of traumatic injury to both the central and peripheral nervous systems by facilitating reconnection and reestablishment of function, decreasing ischemia and neuronal death, and reducing Wallerian degeneration after injury.

Xenotransplantation, the use of cells from different species, has also been suggested as a viable approach to circumventing the limitations associated with human fetal neural transplantation (Galpern W R, et al. 1996 *Experimental Neurology* 140:1–13). Transplant of porcine cells harvested from the midbrains of pig fetuses is currently being evaluated in clinical trials.

Encapsulated xenografts of rat PC12 cells that secrete dopamine have also been developed. A semipermeable polymer membrane allows diffusion of the small therapeutic molecules but prevents diffusion of the larger immunogenic molecules. Whether the release of dopamine from encapsulated sources will be sufficient to restore optimal dopamine levels in Parkinson's Disease patients remains to be determined.

However, while cells derived from non-human animals are potential candidates for human neural transplantation, they carry the risks of transferring intrinsic pathogens, creating novel infectious agents, or eliciting deleterious immune responses (Isacson, O. and Breakefield X. 1997 *Nature Medicine* 3:964–969).

According to Anton et al. (1994 *Exp. Neurol.* 127:207–218), the ideal cell for a CNS transplant system should meet the following criteria: It should be of human CNS origin, capable of growth cessation and differentiation, clonal and defined, transfectable and selectable, immunologically inert, capable of long-term survival following implantation, non-tumorigenic, functional and integrated into the host brain, of consistent quality, and readily available.

The present invention provides neuronal cell transplants useful in studying and treating spinal cord and brain injuries and neurodegenerative disorders.

SUMMARY OF THE INVENTION

The present invention relates to a method of treating an individual suspected of suffering from a disease, condition or disorder characterized by the damage or loss of neurons which comprises implanting a sample from a culture of at least 95% pure, stable, homogeneous post-mitotic human neurons into the individual at or near the site of the damage or loss.

The present invention relates to a method of treating an individual suspected of suffering from an injury, disease, condition or disorder of the Central Nervous System which comprises implanting a sample from a culture of at least 95% pure, stable, homogeneous post-mitotic human neurons into the individual's brain.

The present invention relates to a method of treating an individual suspected of suffering from an injury, disease, condition or disorder to the spinal cord which comprises implanting a sample from a culture of at least 95% pure, stable, homogeneous post-mitotic human neurons into the individual's spinal column.

The present invention relates to a method of treating an individual suspected of suffering from an injury, disease, condition or disorder to nerve cells which comprises implanting a sample from a culture of at least 95% pure, stable, homogeneous post-mitotic human neurons into the individual's body at the site of nerve dysfunction or damage.

The present invention relates to a pharmaceutical composition that comprises a sample from a culture of at least 95% pure, stable, homogeneous post-mitotic human neurons and a pharmaceutically acceptable medium.

The present invention relates to a method of generating a non-human animal model for a human disease, condition or disorder of the Central Nervous System comprising implanting a sample from a culture of at least 95% pure, stable, homogeneous post-mitotic human neurons into a non-human animal.

The present invention relates to an non-human animal comprising a sample from a culture of at least 95% pure, stable, homogeneous post-mitotic human neurons implanted in its brain, nervous system or spinal column.

The present invention relates to a method of obtaining neuronal cells with a selected phenotype comprising co-culturing neuronal cells with astrocytes from a region of the of the central nervous systems exhibiting the selected phenotype.

DETAILED DESCRIPTION OF THE INVENTION

Figure 1A:
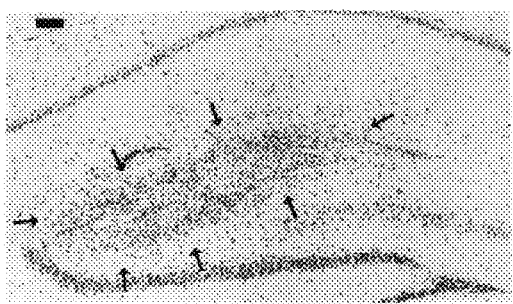
FIG. 1A, FIG. 1B, FIG. 1C, FIG. 1D, FIG. 1E, FIG. 1F, FIG. 1G and FIG. 1H contain photomicrographs of NT2N graft in the hippocampus (dentate gyrus and polymorph layer) 4 weeks post-transplant probed with various monoclonal antibodies.

The present invention relates to compositions and methods relating to transplanting neurons into either individuals who are suspected of suffering from an injury, disease, disorder or condition or into non-human animals to generate a non-human animal model of a human disease, disorder or condition. The neurons used in the methods of the present invention are at least 95% pure, stable, homogeneous post-mitotic human neurons. Optionally, the neurons may comprise exogenous genetic material. The neurons used in the methods of the present invention are genotypically and phenotypically homogeneous.

As used herein, the term "sample" is meant to refer to one or more cells. In preferred embodiments, a sample contains a plurality of cells. According to the present invention, a sample from a culture of at least 95% pure, stable, homogeneous post-mitotic human neurons is implanted into either a non-human animal or a human. Accordingly, the methods of the present invention relate to the implantation of one or more cells from a culture of at least 95% pure, stable, homogeneous post-mitotic human neurons into either a non-human animal or a human.

As used herein, the term "at or near a site of said nerve damage" is meant to refer to the location where nerve cells are implanted in order to replace destroyed, damaged or dysfunctional nerve cells and/or restore function resulting from destroyed, damaged or dysfunctional nerve cells. The location is defined as being a site where such implanted cells can develop as replacement cells for destroyed, damaged or dysfunctional nerve cells and make the necessary linkages to restore function lost due to destroyed, damaged or dysfunctional nerve cells. In a preferred embodiment, by "at or near the site of nerve damage" it is meant that cells are implanted not only at the site at which the nerve cells are actually damaged but also at sites caudal and rostral to the site of damage.

As used herein, the term "exogenous genetic material" refers to genomic DNA, cDNA, synthetic DNA and RNA, mRNA and antisense DNA and RNA which is introduced into the cell or an ancestor cell. The exogenous genetic material may be heterologous or an additional copy or copies of genetic material normally found in the individual or animal. When cells are used as a component of a pharmaceutical composition in a method for treating human injuries, diseases, conditions or disorders, the exogenous genetic material that is used to transform the cells may encode proteins selected as therapeutics used to treat the individual and/or to make the cells more amenable to transplantation. When cells are used in a method for generating non-human animal models of human CNS diseases or disorders, the exogenous genetic material that may be incorporated into the cells may encode proteins selected to create conditions in the non-human animal which simulate or resemble conditions in a human suffering from a CNS disease, condition or disorder to be modeled.

The exogenous genetic material is preferably provided in an expression vector which includes the coding region of a protein, whose production by the cells is desirous, operably linked to essential regulatory sequences such that when the vector is transfected into the cell, the exogenous genetic material is capable of being expressed within the cell.

According to some embodiments of the present invention, a sample from a culture of pure, stable, homogeneous post-mitotic human neurons is transplanted into an individual being treated for a CNS injury, disease, condition or disorder. These cells essentially replace and/or function in place of endogenous damaged, dead, non-functioning or dysfunctioning cells. Thus, in the case of an individual suffering from an injury, disease, condition or disorder characterized by loss, damage or dysfunction of neurons such as, for example, diseases associated with nerve damage or spinal injury, the cells are transplanted into a site in the individual where the transplanted cells can function in place of the lost, damaged or dysfunctional cells and/or produce products needed to improve or restore normal functions that have been reduced or lost due to the lack of such products endogenously produced in the individual. In the case of an individual suffering from a CNS injury, disease, condition or disorder characterized by loss, damage or dysfunction of neurons in the brain, the cells are transplanted into the brain of the individual. The transplanted cells function in place of the lost, damaged or dysfunctional cells and/or produce products needed to improve or restore normal brain functions that have been reduced or lost due to the lack of such products endogenously produced in the individual.

According to some embodiments of the present invention, a sample from a culture of pure, stable, homogeneous post-mitotic human neurons is transplanted into the individual being treated for a disease, condition or disorder in order to provide living neurons which produce desired substances. The transplanted cells may produce specific products that, when present at or near the site of implantation in the treated individual, reverse or impede the pathology associated with the disease, condition or disorder being treated.

According to some embodiments of the present invention, a sample from a culture of pure, stable, homogeneous post-mitotic human neurons is transplanted into a non-human animal in order to provide a model for a human CNS disease, condition or disorder. The transplanted cells may produce products that result in the development of conditions which are similar to or mimic the pathology of a CNS disease or condition.

The method may be used to treat individuals suffering from injuries, diseases, conditions or disorders characterized by the loss, damage or dysfunction of endogenous cells. The method may be used to treat individuals suffering from stroke, spinal injury or other injuries, conditions or disorders associated with neuron damage or death. CNS diseases and disorders which may be treated by practicing the methods of the present invention include any disease of the CNS which is characterized by the loss, damage or dysfunction of endogenous cells, the symptoms of which may be reversed or reduced in severity by providing neurons that can replace such cells and produce products needed for proper function or needed to counteract the presence of compounds that are not normally present or present at abnormal levels. The present invention is useful for the treatment of progressive neurodegenerative disorders such as Alzheimer's disease, Parkinson's disease, Huntington's disease, amyotrophic lateral sclerosis and hereditary ataxia, as well as neurological conditions such as strokes and nerve injuries. The present invention is useful to treat diseases by serving as a delivery system to produce and disseminate active proteins and other active compounds needed for proper brain function.

A pharmaceutical composition according to the present invention useful for treating individuals suffering from injuries, diseases, conditions or disorders characterized by the loss, damage or dysfunction of endogenous cells comprises a sample from a culture of pure, stable, homogeneous post-mitotic human neurons and a pharmaceutically acceptable medium. The neurons used in the present invention must be a stable, homogeneous culture of post-mitotic human neurons that is at least 95% pure. The neurons used in the present invention may be transfected with exogenous genetic material.

The exogenous genetic material used to transform the cells may encode proteins selected as therapeutics for delivery to the brain of the treated individual. Protein products encoded by transfected genetic material include, but are not limited to, those leading to production of neurotransmitters (e.g. tyrosine hydroxylase) as well as neurotrophic substances such as nerve growth factor (NGF), brain-derived neurotrophic factor (BDGF), basic fibroblast growth factor (bFGF) and glial-derived growth factor (GDGF). In addition, tumor suppressor genes such as P53 and thrombospondin can be incorporated into the cells.

According to another embodiment of the present invention, a sample from a culture of pure, stable, homogeneous post-mitotic human neurons are transplanted into the brain of a non-human animal in order to generate a non-human animal model of a human CNS disease, condition or disorder. The presence of the cells bring about changes in the animal's brain such that the animal develops features which resemble or mimic the characteristics of the human CNS disease, condition or disorder. The transplanted cells produce specific products that, when present in the brain of the animal, give rise to conditions which resemble or mimic the pathology associated with the disease being modeled. The cells used to generate the non-human animal models according to the present invention useful for treating CNS diseases comprise a sample from a culture of pure, stable, homogeneous post-mitotic human neurons and a pharmaceutically acceptable medium. The neurons used in the present invention must be a stable, homogeneous culture of post-mitotic human neurons that is at least 95% pure.

CNS diseases and disorders which may be modeled by practicing the methods of the present invention include any disease of the CNS which is characterized by endogenous dead, non-functioning or dysfunctioning cells, particularly those characterized by cells producing proteins not normally associated with the cells or producing normal proteins at abnormal levels. Thus, the transplantation into the brain of an animal of cells which produce proteins associated with a human CNS disease gives rise to conditions which resemble or mimic the characteristics associated with the pathology of the disease or disorder being modeled. The present invention is useful to generate non-human animal models of progressive neurodegenerative disorders such as Alzheimer's disease, Parkinson's disease, Huntington's disease, amyotrophic lateral sclerosis, hereditary ataxia, and motor neuron and Lewy body disease. Many different genes are implicated in these diseases such as normal and mutated amyloid precursor genes, genes encoding kinases, phosphotases, normal and mutated superoxide dismutase, neurofilament proteins and apolipoprotein 4. In addition, specific oncogenes responsible for certain types of cancer can be incorporated to generate animal models for such cancer using the NT2 derived cells.

In some embodiments of the present invention, the neurons used may be produced by a method described in U.S. Pat. No. 5,175,103 issued Dec. 29, 1992, which teaches a method for obtaining >95% pure postmitotic human neurons (termed NT2N cells) from a human teratocarcinoma cell line (termed NTera2/clone PI or NT2 cells) following treatment of the NT2 cells with retinoic acid (RA). In addition to providing a model system for a wide range of biochemical, molecular biological and morphological studies of neurons in vitro, the stable, homogeneous population of pure human neurons may be used in in vivo transplants in order to generate animal models of CNS diseases and disorders or they may be used in in vivo transplants into the brains or spinal cords of individuals suffering from CNS diseases or disorders as therapeutics/prophylactics to introduce neurons which are capable of producing products that reverse or impede the pathology associated with CNS diseases or disorders afflicting the individual.

The NT2 cell line is capable of differentiating into neurons, glia and mesenchymal cells, because the NT2 cells appear to correspond to progenitor cells, the progeny of which are restricted to the neuronal lineage (Abramham, I. et al. 1991 *J. Neurosci. Res.* 28:29–39; Andrews, P. W., et al. 1981 *Tissue Antigens* 17:493–500; Andrews, P. W. et al 1984. 1984 *Lab. Invest.* 50 147–162; Andrews, P. W. 1987. *Devel. Biol.* 103:285–293; Kleppner, S. R., et al 1992 *Soc. Neurosci. Abst.* 18:782; Lee, V. M.-Y. and P. W. Andrews 1986 *J. Neurosci.* 6:514–521; and, Younkin, D. P. et al. 1993 *Proc. Natl. Acad. Sci. U.S.A.* 90:2174–2178). Further characterization of the NT2N cells has shown that these cells most closely resemble CNS neurons (Pleasure, S. J., et al. 1992. *J. Neurosci.* 12:1802–1815). The NT2N cells exhibit other properties of CNS neurons, i.e. they express the 695 amino acid long amyloid precursor protein (APP), produce and secrete the β-amyloid or A4 (β/A4) peptide found in Alzheimer's disease amyloid plaques and bear glutamate receptor channels on their cell surface.

The neurons used in the present invention may be transfected with exogenous genetic material. If produced as described in U.S. Pat. No. 5,175,103, the neurons used in the present invention may be transfected with genetic material prior to induction of differentiation. Methods of transfection are well known and taught in the above-referenced patent. The exogenous genetic material used to transform the cells may encode proteins whose presence within cells of the brain or spinal cord are associated with human diseases, disorders or conditions. Protein products encoded by transfected genetic material include, but are not limited to, normal and mutated amyloid precursor, kinases, phosphotases, normal and mutated superoxide dismutase, neurofilament proteins and apolipoprotein 4 as well as neurotransmitters (e.g., tyrosine hydroxylase) and neurotrophic substances such as nerve growth factor (NGF), brain-derived neurotrophic factor (BDGF), basic fibroblast growth factor (bFGF) and glial-derived growth factor (GDGF).

The exogenous genetic material used to transfect the cells is preferably provided in a vector which includes essential regulatory sequences operably linked to coding sequences such that the transfected genetic material is capable of being expressed within the cell.

Expression vectors that encode exogenous genetic material comprise a nucleotide sequence that encodes a protein to be produced operably linked to regulatory elements needed for gene expression. Accordingly, incorporation of the DNA or RNA molecule into the neuron cell results in the expression of the DNA or RNA encoding the protein and thus, production of the protein.

The exogenous genetic material that includes the nucleotide sequence encoding the protein operably linked to the regulatory elements may remain present in the cell as a functioning episomal molecule or it may integrate into the cell's chromosomal DNA. Exogenous genetic material may be introduced into cells where it remains as separate genetic material in the form of a plasmid. Alternatively, linear DNA which can integrate into the chromosome may be introduced into the cell. When introducing DNA into the cell, reagents which promote DNA integration into chromosomes may be added. DNA sequences which are useful to promote integration may also be included in the DNA molecule. Alternatively, RNA may be introduced into the cell.

The necessary elements of an expression vector include a nucleotide sequence that encodes a protein and the regulatory elements necessary for expression of that sequence in the cells. The regulatory elements are operably linked to the nucleotide sequence that encodes the protein to enable expression. The nucleotide sequence that encodes the protein may be cDNA, genomic DNA, synthesized DNA or a hybrid thereof or an RNA molecule such as mRNA.

The regulatory elements necessary for gene expression include: a promoter, an initiation codon, a stop codon, and a polyadenylation signal. It is necessary that these elements be operable in the neurons. Moreover, it is necessary that these elements be operably linked to the nucleotide sequence that encodes the protein such that the nucleotide sequence can be expressed in the neuron cells and thus the protein can be produced.

Initiation codons and stop codon are generally considered to be part of a nucleotide sequence that encodes the protein. However, it is necessary that these elements are functional in the neurons.

Similarly, promoters and polyadenylation signals used must be functional within the neuron cells.

Examples of promoters useful to practice the present invention include but are not limited to cytomegalovirus promoter, particular the immediate early promoter, SV40 promoter and retroviral promoters.

An example of a polyadenylation signal useful to practice the present invention is the SV40 polyadenylation signal.

An additional element may be added which serves as a target for cell destruction if it is desirable to eliminate transplanted cells for any reason. For example, an expressible form of a herpes thymidine kinase (tk) gene can be included in the exogenous genetic material. When the exogenous genetic material is introduced into the neuron, tk will be produced. If it is desirable or necessary to kill the transplanted cells, the drug gancyclovir can be administered to the individual and that drug will cause the selective killing of any cell producing tk. Thus, a system can be provided which allows for the selective destruction of transplanted cells.

In order for exogenous genetic material in an expression vector to be expressed, the regulatory elements must be operably linked to the nucleotide sequence that encodes the protein. Accordingly, it is necessary for the promoter and polyadenylation signal to be in frame with the coding sequence. In order to maximize protein production, regulatory sequences may be selected which are well suited for gene expression in the neuronal cells. Moreover, codons may be selected which are most efficiently transcribed in the cell. One having ordinary skill in the art can produce exogenous genetic material as expression vectors which are functional in neurons.

Neurons may be transplanted into individuals suspected of suffering from injuries, diseases, conditions or disorders characterized by the damage or loss of neurons at the site of such neuron injury or loss by direct grafting of neurons at the site of neuron injury or loss. Neurons may be transplanted into the brains of individuals suspected of suffering from CNS diseases, conditions or disorders by direct grafting of neurons into the brains of such individuals. Additionally, neurons may be transplanted into the brains of individuals suffering from head trauma or strokes. Individuals suspected of or identified as suffering from diseases, conditions, disorders, or injuries rendering neurons in the brain damaged, destroyed or dysfunctional may be treated by implantation of neurons to replace or compensate for the loss of neuron function due to the destruction or dysfunction of endogenous neurons.

In some embodiments, $1\times10^3$ to $1\times10^6$ neurons are implanted. In some embodiments, $5-10\times10^4$ neurons are implanted. Two techniques have been used for neural transplantation. The first comprises stereotaxic surgery in which a neuron cell suspension is implanted into the brain. The second comprises a microsurgical procedure in which the cells are grafted into the brain. Techniques for transplanting neural tissue are disclosed in: Backlund, E.-O. et al., (1985) *J. Neurosurg.* 62:169–173; Lindvall, O. et al. (1987) *Ann. Neurol.* 22:457–468; and Madrazo, I. et al. (1987) *New Engl. J. Med.* 316:831–834; each of which is incorporated herein by reference.

Neurons may be implanted into the spinal cord at or near the site of nerve damage from disease or injury. The implanted cells further differentiate into motor neurons, thereby replacing or reconnecting nerves at the site of damage. In some embodiments, the injury is to a motor neuron which is part of the spinal cord. In some embodiments, the injury is to a motor neuron outside the spinal column. Neurons of the invention are implanted at the site of the nerve cell injury, i.e., in proximity to the injured cell or cells at a location where differentiation of implanted cells can replace nerve function and reconnect nerves of the individual to remedy or otherwise ameliorate the injury. The neurons are implanted in a location that allows processes which develop therefrom to substitute for the processes of the damaged nerve, thereby repairing the damaged nerve network. Experiments have demonstrated that phenotypic changes in NT2N cells occur to the greatest extent in transplanted cells in direct contact with host cells. Thus, in a preferred embodiment, NT2N cells are transplanted at multiple locations including not only the site of injury, but also sites caudal and rostral to the site of injury.

Neurons may be transplanted into the brains of non-human animals by injection of neurons into one hemisphere using a stereotaxic instrument and a hand-held 10 ml Hamilton syringe. Aliquots of $1\times10^3$ to $1\times10^6$ neurons are injected into the adult and neonatal rats. In some embodiments, $5-10\times10^4$ neurons are injected. For the adult rats, cells are injected stereotaxically into cerebral cortex, subjacent white matter or hippocampus at one site in a single hemisphere of each rat.

Neurons may also be transplanted into the spinal cord of animals including humans at or near an injured site. In a preferred embodiment at least $2\times10^6$ cells are engrafted into a lesion. It is preferred that these cells be split among at least three locations which include the site of injury and sites caudal and rostral to the site of injury. In this embodiment, approximately one-half of the cells are applied via syringe to the caudal and rostral ends of the spinal cord. The other half of the cells ($10^6$) are inserted at the site of injury. In a preferred embodiment, these cells are incorporated into a resorbable gel for parenteral use, such as MATRIGEL, which keeps the cells spread through the lesion where they appear to secrete trophic factors which help cell processes cross from either end into the center.

The present invention is further illustrated by the following examples, which are not intended to be limiting in any way.

EXAMPLES

Example 1

NT2N Cell Transplantation into Brains of Mice:

Studies of NT2N cells transplanted into the brains of nude mice show that these NT2N cells integrate as neurons into the brains of immunodeficient nude mice where they survive >12 months without evidence of rejection or tumor formation. Furthermore, transplantation of NT2N neurons in cyclosporine-treated and untreated immunocompetent Sprague-Dawley rats has been performed and survival of the cells has been observed.

The following is a review of experiments demonstrating implantation of neuronal cells into brains of immunocompetent animals.

MATERIALS AND METHODS

Culture of NT2 cells and generation of NT2N neurons were performed essentially as described in U.S. Pat. No. 5,175,103. Briefly, NT2 cells were cultured using standard techniques and were passaged 1:3 twice per week in Opti-MEM with 5% fetal bovine serum and penicillin/streptomycin. NT2 cells were induced to differentiate into neurons by administration of 10 $\mu$m retinoic acid (RA), which was replenished twice weekly, for 5 weeks at which time the cells were replated to establish Replate 1 cells.

Highly differentiated NT2N cells were then obtained following two subsequent replate manipulations (designated Replate 2 and Replate 3) at which time the NT2N cells were >99% pure. Freshly harvested aliquots of Replate 3 NT2N neurons were washed three times in buffer and then used in the transplantation studies described here.

Additionally, in experiments conducted in 2 rats, previously frozen aliquots of NT2N cells were thawed immediately prior to injection into the CNS.

Implantation Of NT2N Cells Into Rat Brain:

Adult (170–280 gm) female Sprague/Dawley rats were anesthetized by intraperitoneal injections of Ketamine (87 mg/kg) and Xylazine (13 mg/kg), prepared for surgery and placed in a stereotaxic instrument (Kopf, Tujunga, Calif.). Neonatal (postnatal day 5) female Sprague/Dawley rats were anesthetized by hypothermia during the injection of NT2N cells into one hemisphere using a stereotaxic instrument and a hand-held 10 µl Hamilton syringe. Aliquots of $5-10 \times 10^4$ NT2N cells were injected into the adult and neonatal rats. For the adult rats, NT2N cells were injected stereotaxically into cerebral cortex, subjacent white matter or hippocampus at one site in a single hemisphere of each rat. A total of 68 rats were used in this study (see Table 1).

The stereotaxic injection sites were determined using system B of Pellegrino et al. (Pellegrino, L. J., et al. 1979. A Stereotaxic Atlas Of The Rat Brain, Plenum Press, New York) and all of the injections were performed by injecting 2 µl of a suspension of the NT2N cells over 5 min. After the injection, the needle was left in place for another 5 min. and then slowly removed. The viability of the NT2N cells before they were injected was monitored microscopically using Tryptan blue exclusion. Similar procedures were used to monitor the viability of residual, uninjected NT2N cells after the transplantation procedure had been completed.

A subset of the adult rats (N=13) implanted with NT2N cells were treated daily by the oral (N=8; using a gavage tube) or subcutaneous (N=5) administration of cyclosporine (7–10 mg/kg per day) for the duration of their survival post-transplantation.

Following different post-transplantation survival times, the rats were deeply anesthetized and sacrificed by perfusion with phosphate buffered saline (to wash out red blood cells and serum proteins) followed by 70% ethanol and 150 mM NaCl. The brains were removed and fixed by overnight immersion in 70% ethanol and 150 mM NaCl. The post-transplant survival times ranged from 4 days to 21 weeks as summarized in Table 1.

Table 1 summarizes data on the number of adult (with and without subcutaneous or oral cyclosporine treatment) and neonatal rats used for transplantation as well as the survival times post-transplantation for each group of rats (left and middle columns). The number of rats with viable NT2N grafts is shown in the far right column. The number of rats treated with subcutaneous (sc) cyclosporine is indicated in parentheses.

Immunohistochemical Procedures:

The methods for tissue processing and light microscopic immunohistochemical analysis are well known. Antibodies were used for the immunohistochemical characterization of the NT2N grafts. Both monoclonal and polyclonal antibodies to neuronal and glial cytoskeletal proteins and other polypeptides that have been shown to serve as molecular signatures of the neuronal or glial phenotype were selected to identify and characterize the NT2N grafts. These antibodies have been extensively characterized and their properties are summarized in Table 2.

Specifically, Table 2 summarizes the properties of the 27 different antibodies used in this study and their reactivity with NT2N cells grafted into the rat brain. The far left column indicates the polypeptide recognized by the antibody which is named in the second column. The third column gives the dilution or immunoglobulin concentration of each antibody as it was applied here. The fourth column indicates whether or not the antibody stained grafted NT2N cells (+positive; -—negative; +/-—weak or equivocal staining). The antibodies are grouped together according to the cell types in which they are predominantly or exclusively expressed.

The abbreviations used in the first column of the Table 2 (in alphabetical order) are:

GFAP=Glial fibrillary acid protein;
MAP2=Microtubule-associated protein 2;
MAP5=Microtubule-associated protein 5;
MBP=myelin basic protein;
N-CAM=Neural-cell adhesion molecule;
NF=Neurofilament;
NF-L=Low molecular weight NF protein;
NF-M=Middle molecular weight NF protein;
NF-H=High molecular weight NF protein;
p75 NGFR=Low affinity (75 kD) nerve growth factor receptor;
$p^{ind}$=Phosphate independent epitope in NF-L or NF-H;
P−=Non- or poorly phosphorylated epitope in NF-H or NF-M;
P+=Moderately phosphorylated epitope in NF-H;
P+++=Heavily phosphorylated epitope in NF-H;
PHF=Paired helical filaments in Alzheimer's disease neurofibrillary tangles.

Note that two antibodies (i.e., T3P and PHF1) to tau proteins recognize fetal tau and the abnormally phosphorylated tau proteins (at serine number 396 according to the numbering system for the 441 amino acid long tau protein) in PHFs (also known as A68 proteins), but not normal adult tau. Note that although the anti-CFAP and anti-macrophage MAbs stained occasional reactive astrocytes and macrophages, respectively, that had infiltrated the graft, the NT2N cells themselves were not stained by these MAbs.

RESULTS

Figure 1B:
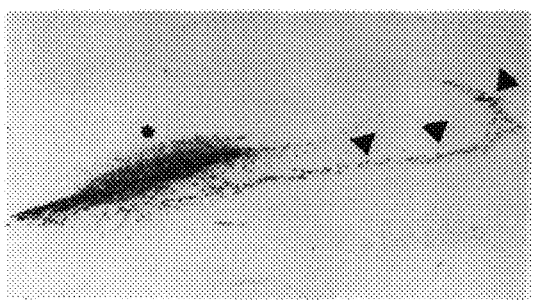
Figure 1C:
Figure 1D:
Figure 1E:
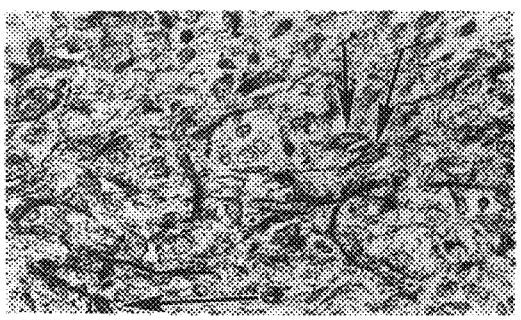
Figure 1F:
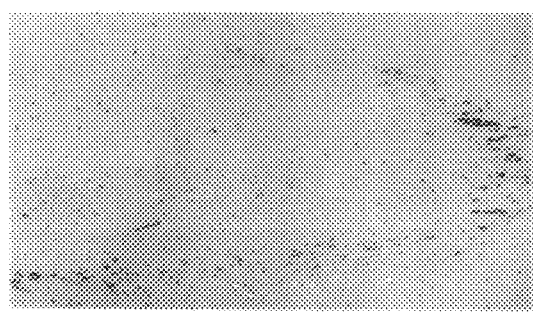
Figure 1G:
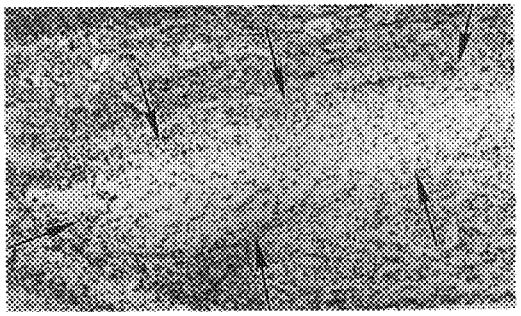
Figure 1H:
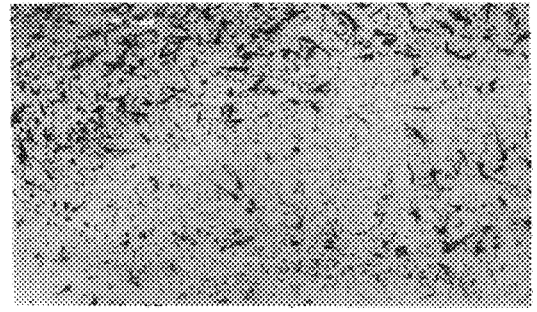

Specific Identification Of NT2N Grafts With Monoclonal Antibodies:

FIG. 1A and FIG. 1B contains photomicrographs of NT2N graft in the hippocampus (dentate gyrus and polymorph layer) 4 weeks post-transplant. FIG. 1A shows a low power view of a Cresyl Violet stained section of the NT2N graft (delineated by the arrows). FIG. 1B shows a low power view of the same NT2N graft stained with the human specific anti-N-CAM MAb (MOC 1). The asterisk lies above the portion of the graft containing the perikarya and simple dendritic arbor of the NT2N neurons while the arrow heads identify the axons emanating from the graft and extending in the mossy fiber pathway dorsal to pyramidal neurons in CA3. The region identified by the asterisk is shown at higher power in FIG. 1C and the segment of graft-derived axons located below the middle arrow head is shown at higher power in FIG. 1D. Note that only the NT2N neurons and their processes are stained by this MAb. FIG. 1A and FIG. 1B are at the same magnification and the bar in FIG. 1A=100 µm. FIG. 1C and FIG. 1D show a higher power views of the NT2N graft stained by the human specific anti-N-CAM MAb (MOC1 ). Note that the NT2N neurons and some of their dendrites (FIG. 1C) as well as their axons (FIG. 1D) are stained, but not the endogenous rodent N-CAMs. The photomicrographs in FIG. 1C, FIG. 1F, FIG. 1G and FIG. 1H are all at the same magnification and the bar in FIG. 1C=100 μm, while FIG. 1D and FIG. 1E are taken at a slightly higher magnification and the bar in FIG. 1C corresponds to 25 μm in FIG. 1D and FIG. 1E. FIG. 1E and FIG. 1F show regions similar to those illustrated in FIG. 1C and FIG. 1D, respectively, in an adjacent section stained with the MAb RHdO20 (FIG. 1D) to poorly phosphorylated NF-H/M and the MAb HO14 (FIG. 1F) to moderately phosphorylated isoforms of NF-H. FIG. 1G shows results obtained with a MAb to highly phosphorylated NF-H (RMO24) which stains only endogenous rat axons, but not the NT2N graft (arrows) despite the fact that RMO24 also recognizes human NF-H. The section shown in FIG. 1H is adjacent to that seen in FIG. 1F and it was probed with the MAb to GFAP. Some reactive astrocytes infiltrate the graft similar to the colonization of dorsal root ganglion grafts transplanted into rat brain, but most CFAP positive reactive astrocytes surround the graft. The sections in FIG. 1B–FIG. 1H were lightly counterstained with hematoxylin.

Figure 2A:
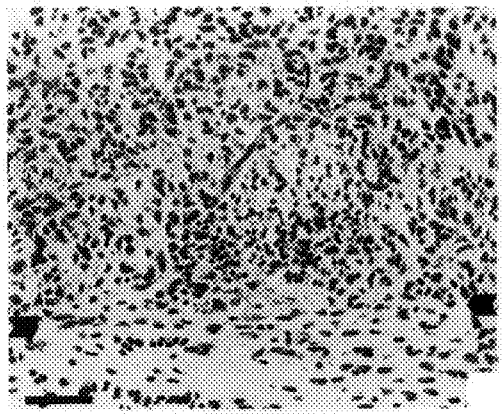
FIG. 2A, FIG. 2B and FIG. 2D show photomicrographs of three different NT2N grafts in the subcortical white matter and the dorsal diencephalon (FIG. 2C) 2–4 weeks post-transplant stained with Cresyl Violet (FIG. 2A, FIG. 2C and FIG. 2D) or the MAb (ED1) to macrophages (FIG. 2B).
Figure 2B:
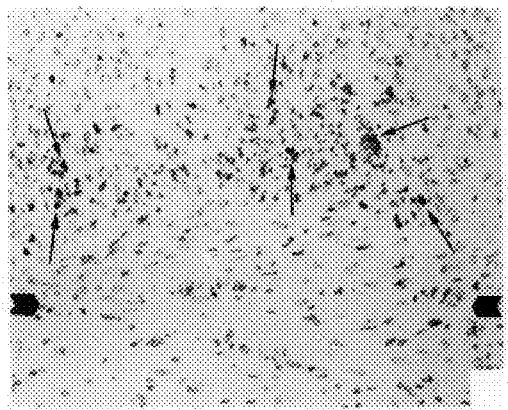
Figure 2C:
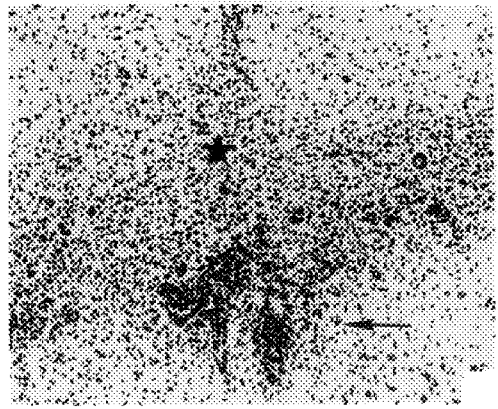
Figure 2D:
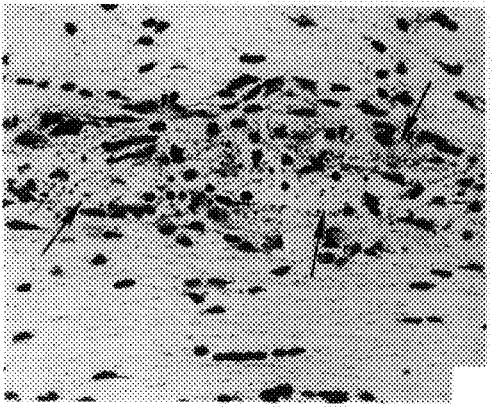

FIG. 2A, FIG. 2B, FIG. 2C and FIG. 2D show photomicrographs of three different NT2N grafts in the subcortical white matter (FIG. 2A, FIG. 2B and FIG. 2D) and the dorsal diencephalon (FIG. 2C) 2–4 weeks post-transplant stained with Cresyl Violet (FIG. 2A, FIG. 2C and FIG. 2D) or the MAb (ED1) to macrophages (FIG. 2B). FIG. 2A and FIG. 2B are adjacent sections of the same graft and the arrow heads identify the interface between the graft (above) and the subjacent white matter (below). FIG. 2A and FIG. 2B are at the same magnification and the bar in FIG. 2A=50 μm. The arrows in FIG. 2B identify ED1 positive macrophages in an area of the graft containing some NT2N neurons undergoing focal karyorrhexis. More extensive inflammation is seen around blood vessels in FIG. 2C (arrow) at the margin of the graft (star) while more severe karyorrhexis of grafted NT2N cells is seen in another subcortical white matter NT2N graft shown in FIG. 2D where the arrows identify accumulations of nuclear debris. FIG. 2C and FIG. 2D are at different magnifications and the bar in FIG. 2A corresponds to 100 μm in FIG. 2C and to 30 μm in FIG. 2B.

Figure 3A:
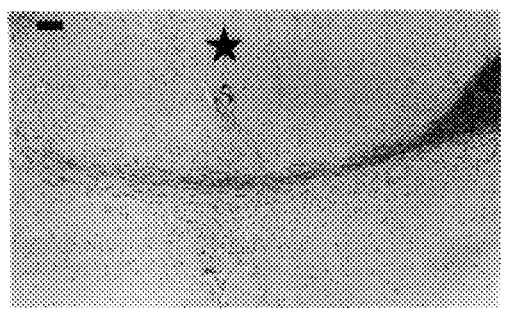
FIG. 3A, FIG. 3B, FIG. 3C, FIG. 3D, FIG. 3E, FIG. 3F, FIG. 3G and FIG. 3H contain photomicrographs of an NT2N graft in the subcortical white matter at 4 weeks post-transplant probed with MAbs and counterstained with hematoxylin.
Figure 3B:
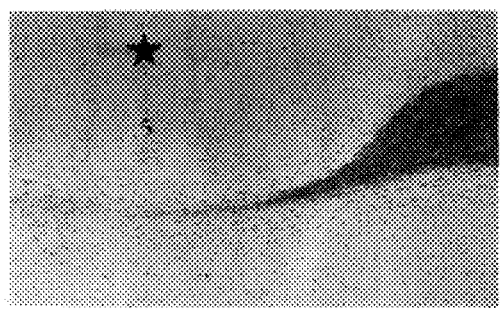
Figure 3C:
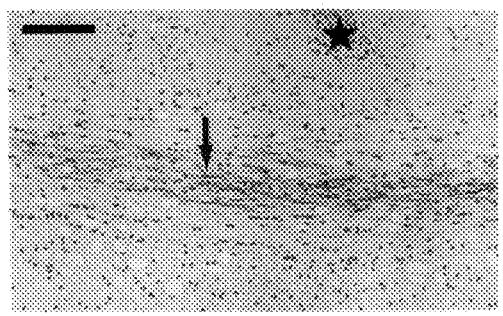
Figure 3D:
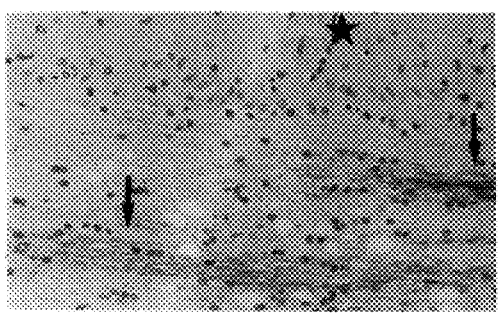
Figure 3E:
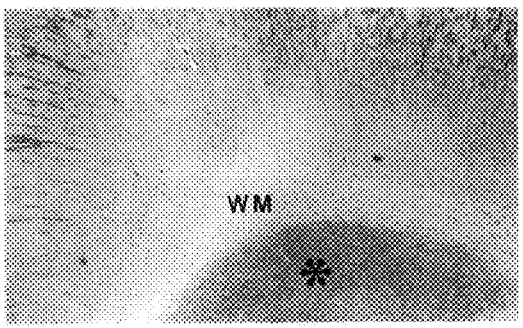
Figure 3F:
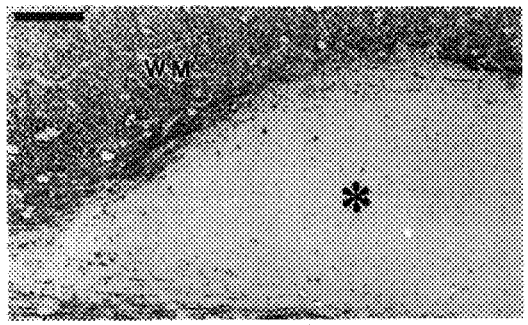
Figure 3G:
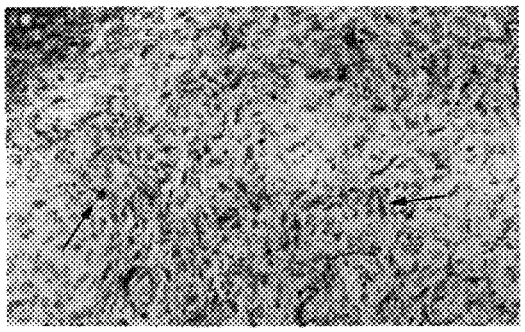
Figure 3H:
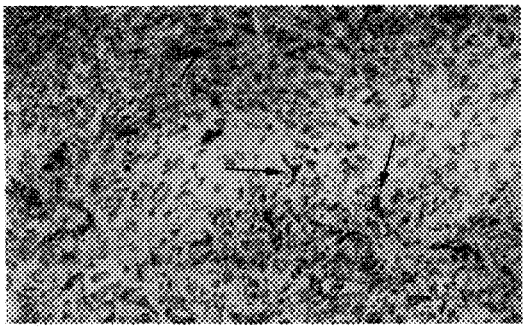

FIG. 3A, FIG. 3B, FIG. 3C, FIG. 3D, FIG. 3E, FIG. 3F, FIG. 3G and FIG. 3H contain photomicrographs of an NT2N graft in the subcortical white matter at 4 weeks post-transplant probed with MAbs and counterstained with hematoxylin. The section shown in FIG. 3A was stained with the human specific anti-NF-H MAb (H014) which demonstrates the grafted perikarya and their dendrites in the NT2N transplant to the right in the figure. Labeled axons extend medially from the graft site to the left in this panel. Note that these axons cross the midline (star) within the corpus callosum. The section in FIG. 3B, which was a section adjacent to that shown in FIG. 3A, was probed with a MAb to human N-CAM (MOC1) which stains the somatodendritic domain of NT2N cells in the graft to the right in this figure as well as axons that cross the midline (star) to the left within the corpus callosum. FIG. 3A and FIG. 3B are at the same magnification and the bar in FIG. 3A=100 μm. The axons in the corpus callosum seen in FIG. 3A and FIG. 3B are shown at higher power in FIG. 3C and FIG. 3D, respectively. These axons (arrows in FIG. 3C and FIG. 3D) cross the midline (star in FIG. 3C and FIG. 3D) to the hemisphere contralateral to the NT2N graft. FIG. 3C and FIG. 3D are at different magnifications and the bar in FIG. 3C=100 μm while the same bar corresponds to 50 μm in FIG. 3D. In FIG. 3E, the MAb to MAP2 (AP14) labels the somatodendritic domain of the grafted NT2N neurons. The cell body mass of the graft is identified by an asterisk and the overlying white matter (WM) is unstained. The somatodendritic domain of endogenous host neurons in the overlying cortex also are labeled in this section and labeled apical dendrites are most prominent at this magnification. FIG. 3E is at the same magnification as FIG. 3A and FIG. 3B. In FIG. 3F, the MAb to highly phosphorylated NF-H (RHO24) does not stain the NT2N neurons and their processes in the graft (asterisk). However, endogenous axons in the surrounding white matter (WM) are labeled by this MAb thereby delineating the extent of the cell body mass and dendrites of this graft. The bar in FIG. 3F=100 μm. The two photomicrographs shown in FIG. 3G and FIG. 3H are high power views of the NT2N grafts in adjacent sections stained with the anti-NF-L antiserum (FIG. 3G) and the MAb (TA51) to moderately phosphorylated isoforms of NF-H (FIG. 3H). Note that many of the NT2N neurons contain immunoreactive NF-L and NF-H (arrows in FIG. 3G and FIG. 3H, respectively) in their perikarya and processes. Additionally, endogenous rodent axons in the white matter (upper left in FIG. 3G and FIG. 3H) also are labeled by these antibodies. FIG. 3G and FIG. 3H are at the same magnification and the bar in FIG. 3F corresponds to 50 μm in FIG. 3G and FIG. 3H.

Although the grafts could be recognized in Cresyl Violet stained sections (FIG. 1A, FIG. 2A, FIG. 2B and FIG. 2D), the identification of transplanted NT2N cells in the rodent CNS was greatly facilitated by exploiting the restriction of certain polypeptides or epitopes contained within some of these polypeptides to human versus rat and mature versus immature CNS neurons. For example, MOC1, the monoclonal antibody (MAb) to human neural cell adhesion molecules (N-CAMs), was shown to recognize N-CAMs in the human NT2N neurons, but not the N-CAMs in the rat CNS (FIG. 1B–FIG. 1D). Indeed, the cytology of the NT2N cells was not sufficiently-distinctive to allow recognition of the NT2N cells without the use of immunohistochemistry. Furthermore, axons arising from the NT2N grafts were only identifiable as graft derived when they were labeled with the human polypeptide specific antibodies described here (FIG. 1B, FIG. 1F, FIGS. 3A–3D). In addition to the anti-N-CAM MAb, the grafted NT2N cells also could be specifically identified with the MAb H014, an antibody that recognizes moderately phosphorylated isoforms of the middle (NF-M) molecular weight (Mr) neurofilament (NF) subunit in the human CNS and in NT2N cells, but not in the rodent CNS (FIG. 1F). In contrast, RMO24 (FIG. 1G) and RMO217, both of which are MAbs to the most heavily phosphorylated isoforms of the high (NF-H) Mr NF subunit that appear only in mature CNS neurons, immunostained NF-H in rodent CNS neurons, but these MAbs did not stain the human NT2N cells in the grafts described here. The inability of RMO24 and RM0217 to stain the grafted NT2N cells probably reflects the incomplete phosphorylation of NF-H in the grafted NT2N cells (which reflects the incomplete maturation of these grafted neurons), since both MAbs recognize phosphorylated NF-H extracted from the fully mature, human CNS. If the NT2N cells are allowed to survive for an extended period of time (i.e., >6 months) in the immunodeficient nude mouse brain, then the grafted NT2N neurons acquire the most heavily phosphorylated isoforms of NF-H and these fully mature grafted neurons are labeled by RMO24 and RMO217. However, grafted NT2N cells were only studied here for post-transplant survival times of <4 months, and both RMO24 and RMO217 strongly stained rat CNS neurons, but not the grafted NT2N cells, and MOC1 and HO14 stained the NT2N grafts specifically and intensely, but not rat CNS neurons or other rat CNS cells.

Thus, all 4 of these MAbs were used to screen sections from all 68 rats that received implants of the NT2N cells in order to specifically identify the surviving NT2N grafts. Additionally, a MAb (2.2B10) to glial fibrillary acidic protein (GFAP) stained reactive astrocytes surrounding the graft (FIG. 1H) which also helped to delimit the NT2N grafts. Some of these reactive astrocytes infiltrated the NT2N grafts (FIG. 1H) similar to the colonization of dorsal root ganglion grafts by reactive astrocytes transplanted into the rat brain. Screening the graft sites with this panel of MAbs provided a highly effective strategy for identifying grafted NT2N cells even when they existed as small clumps trapped in the leptomeninges or in the needle track dorsal to the injection site.

Survival Of Grafted NT2N Cells:

Nearly all of the transplanted NT2N cells were accurately implanted into neocortex, subjacent white matter and hippocampus although a few also were detected in the diencephalon, the lateral ventricle or within the leptomeninges overlying the neocortical injection site. The number and disposition of the grafted NT2N cells varied from rat to rat, but NT2N grafts were identified immunohistochemically in 100% of adult (N=5) and neonatal (N=5) rats that survived for up to 2 weeks without cyclosporine treatment (see Table 1 for a summary of these and the following data on NT2N graft survival). This group of rats with viable NT2N grafts included 2 rats treated with cyclosporine that had been implanted with aliquots of previously frozen NT2N cells. At the next post-transplant survival interval, i.e., 4 weeks, 10/24 adult and 2/2 neonatal rats that were not treated with cyclosporine contained NT2N brain grafts (Table 1), and many of the transplanted cells resembled small stellate neurons morphologically and histochemically in Nissl stained preparations of the grafts. However, at subsequent post-transplant survival times, only 1 of 19 adult or neonatal rats that were not treated with cyclosporine contained identifiable, surviving NT2N neurons. These findings reflect rejection of the NT2N grafts rather than the cessation of expression of N-CAMs and NF proteins by the grafted NT2N cells. This conclusion is based upon 4 reasons:

1) inflammatory cells were detected in some of the viable grafts in association with cellular debris as early as 2 weeks post-transplantation (FIG. 2C) and many of these inflammatory cells were identified as macrophages using the macrophage specific ED1 MAb (FIG. 2B);

2) cyclosporine prolonged the survival of all NT2N grafts in rats that received this agent by a subcutaneous route;

3) the maximum number of macrophages and inflammatory cells were noted to infiltrate the graft site at 2–4 weeks post-transplantation; and 4) in the immuno-deficient nude mouse, grafted NT2N cells survive >12 months, continue to express N-CAMs and NF proteins, and progressively mature such that they acquire a fully mature neuronal phenotype by 12 months post-transplant.

Of the 5 rats that received subcutaneous cyclosporine, all 5 contained viable NT2N grafts at post-transplant intervals that ranged from 2 to 12 weeks. In contrast, administration of cyclosporine by gavage at the same dose (i.e., 7–10 mg/kg) appeared less effective in preventing graft rejection since only 2 of 8 rats treated in this manner contained an identifiable NT2N graft (Table 1). Notably, the administration of cyclosporine to these rats did not appear to have any detectable effect on the ability of the surviving NT2N cells to express a range of neuronal polypeptides.

Maturation Of Grafted NT2N Cells And The Establishment Of Neuronal Polarity:

Presumably, as a result of their progressive maturation in vivo, NT2N grafts that survived 2–4 weeks post-transplantation were the largest and the most amenable to serial section immunohistochemical analysis, while only a limited number of sections containing identifiable NT2N cells could be obtained from rats that survived 4 days to 1 week post-transplantation. For this reason, studies were focused on the maturational state and polarity of the NT2N cells on rats that survived 2–4 weeks post-transplantation. At these time points, NT2N cells in hippocampus or in the subcortical white matter (which consistently contained larger populations of NT2N cells than the neocortex perhaps due to leakage of the NT2N cells from the cortical injection site into the overlying subarachnoid space) expressed several well characterized polypeptides (e.g., NF subunits and other neuronal cytoskeletal proteins, synaptic polypeptides) that unequivocally identified the NT2N cells as neurons (see FIGS. 3A–3E, FIG. 3G, FIG. 3H and Table 2). However, these neurons resembled late fetal human spinal cord (i.e., >25 weeks gestational age) or young postnatal human cerebellar (i.e., <1 year old) neurons rather than fully mature neurons of the adult CNS in that they failed to acquire heavily phosphorylated isoforms of NF-H. In contrast, polypeptides expressed by glial cells were infrequent in these grafts and the presence of rare GFAP positive astrocytes in these grafts (FIG. 1H) undoubtedly reflects the migration of reactive rat astrocytes into the grafts.

Four week old NT2N neurons extended axons over several millimeters (FIGS. 1B–1F), and some of these axons projected to the hemisphere contralateral to the graft site (FIGS. 3A–3D). Although dendrites were readily identified because they could be labeled with antibodies to microtubule associated proteins (MAPs) restricted to the somatodendritic domain (e.g., MAP2), these dendrites were short with a simplified branching pattern (FIG. 3E). Nonetheless, the presence of identifiable axons and dendrites containing polypeptides that were compartmentalized like their counterparts in authentic rat or human neurons in vivo (FIGS. 1B–1F and FIGS. 3A–3E, FIG. 3G and FIG. 3H) indicate that by 4 weeks post-transplantation the grafted NT2N neurons had acquired the molecular phenotype and structural polarity seen in nearly mature human CNS neurons in vivo. Further, none of the grafted NT2N cells expressed proteins (e.g., nestin, vimentin, p75 NGFR) that are found in neuronal progenitor cells or very immature (i.e., "nascent") human CNS neurons. Significantly, despite evidence of neuronal degeneration due to graft rejection (FIGS. 2A–2D), none of the grafts showed evidence of neuronal cytoskeletal protein abnormalities similar to those seen in common neurodegenerative diseases. Finally, there was no evidence (e.g. mitoses, metastases) to indicate that any of the surviving NT2N cells reverted to a neoplastic phenotype.

DISCUSSION

This study demonstrates the properties of CNS transplants of pure populations of clonal human neuron-like cells that are capable of undergoing progressive, normal maturation and integration into the host mammalian brain without evidence of tumor formation. Only one other CNS cell line, the human HCN-1 line, appears to exhibit an exclusive in vitro commitment to the neuronal lineage, but this cell line does not maintain a stable neuronal phenotype when transplanted into the CNS of experimental animals (Ronnett, C. V. et al. 1990 Science 248:603–605.

The paucity of suitable neuronal cell lines for transplantation has limited studies of the immunological response of the CNS to transplanted neurons alone. This report demonstrates that the NT2N neurons are capable of expressing antigens that induce rejection by about 4 weeks post-transplant. Although the precise nature of these antigens in the NT2N cells is unknown at this time, human teratocarcinoma cell lines similar to the NT2 parent cell line have been shown to express major histocompatibility antigens such as HLA-A, B and C antigens and ($\beta_2$ microglobulin.

More significantly, this study demonstrates that transplanted NT2N neurons are capable of undergoing partial neuronal maturation in the rat brain. The NT2N cells injected into the rat brain progressively matured to about the same extent as their in vitro counterparts maintained in culture for up to 28 days following Replate 3. However, they did not attain the same level of maturity as transplanted NT2N cells that survived for >9–12 months in the immunodeficient nude mouse brain. Specifically, the NT2N grafts in the rat brain did progress to a level of maturation by 4 weeks post-transplant that corresponded to the maturational state of authentic human neurons in the late embryonic spinal cord or in the immature, young postnatal cerebellum. They differ significantly from olfactory sensory neurons and the neuron-like tumor cells in CNS medulloblastomas. However, the transplanted and cultured NT2N cells do resemble the differentiated and fairly mature neurons that have been observed in situ in some teratocarcinomas and many teratomas.

Based on the findings presented here, the transplantation of the NT2N cells into experimental animals can be exploited for several types of unique studies of the developmental biology of neurons and the regressive neurodegenerative events that occur in some neurological disorders. First, the ability to "re-start" the process of neuronal maturation and the development of neuronal polarity by transplanting the NT2N cells into different regions of the rodent brain can be used as models of these two important developmentally regulated processes. The availability of an effective human model system to study these processes in a controlled experimental setting should greatly facilitate efforts to gain insights into the regulatory mechanisms that govern these processes. This model system also will allow the opportunity to explore the possibility that the microenvironment of the host brain might induce NT2N cells grafted into different neuroanatomical sites to assume a region specific morphological and neurotransmitter phenotype.

Moreover, wild type or genetically modified NT2N cells can be used to develop animal models of humans diseases, conditions and disorders, particularly nervous system diseases. For example, the NT2N cells preferentially express the 695 amino acid long Amyloid precursor protein (APP$_{695}$) and they secrete the $\beta$/A4 peptide into the culture medium. Hence, the wild type NT2N cells, NT2N cells transfected to overexpress APP$_{695}$, or NT2N cells transfected to overexpress $\beta$/A4 can be transplanted in order to provide an animal model that releases APP$_{695}$ or $\beta$/A4 into the extracellular space following transplantation. The deposition of $\beta$A4 peptides that occur in the Alzheimer's disease brain can be modeled in this way.

Transplantation of NT2N cells genetically engineered to produce bioactive molecules can be used to develop novel methods to circumvent the blood-brain barrier for the treatment of human neurodegenerative diseases. For example, in view of the therapeutic promise evidenced by recent studies of the use of fetal mesencephalic grafts for the treatment of Parkinson's disease, induction or handling of NT2N cells to acquire or maintain a dopaminergic phenotype for use in the treatment of Parkinson's disease followed by transplantation can be a therapy for individuals suspected of suffering from Parkinson's disease.

Example 2

Transfection and Staining for $\beta$-galactosidase:

Highly purified populations of neurons from a human teratocarcinoma cell line were obtained as described in U.S. Pat. No. 5,175,103. When undifferentiated, the NT2 cells were transfected with 100 $\mu$g SPUD1 and 10 $\mu$g of pSV2neo by lipofection using LIPOFECTIN transfecting reagent (Bethesda Research Laboratories). SPUD1 is a $\beta$-galactosidase expression vector which utilizes the SV40 promoter and has Moloney murine leukemia virus long terminal repeats upstream and downstream. After two days in complete medium, the transfectants were selected with 200 $\mu$g/ml G418 (Gibco) for seven days. Cells were stained for $\beta$-galactosidase activity with 1 mg/ml X-gal, 5 mM potassium ferrocyanide, 5 mM potassium ferricyanide, 2 mM MgCl$_2$ in PBS after fixation in 2% paraformaldehyde, 0.2% glutaraldehyde in phosphate buffered saline pH 7.4. $\beta$-gal positive cultures were subcloned twice and the subclones were used for further studies. The cells were photographed using Hoffman modulation contrast to allow the simultaneous visualization of the blue reaction product and the processes.

The $\beta$-galactosidase ($\beta$-gal) expression plasmid was shown to be present in both undifferentiated and post-mitotic cells. Thus, transfection of expression plasmids into undifferentiated cells allows the introduction of exogenous genetic material into cells. The cells can then be induced to become stable, post-mitotic human neurons and can express the exogenous genetic material.

TABLE 1

POST-TRANSPLANTATION SURVIVAL DATA FOR GRAFTED NT2N CELLS

| Post-transplant survival | Number Of Rats injected w/NT2N Cells | Number Of Rats with viable NT2N cell grafts |
|---|---|---|
| ADULT UNTREATED RATS | | |
| 4 Days | 3 | 3 |
| 2 Weeks | 2 | 2 |
| 4 Weeks | 24 | 10 |
| 6 Weeks | 4 | 0 |
| 8 Weeks | 3 | 1 |
| 13 Weeks | 2 | 0 |
| | SUBTOTAL = 38 | SUBTOTAL = 16 |
| NEONATAL UNTREATED RATS | | |
| 1 Week | 2 | 2 |
| 2 Weeks | 3 | 3 |
| 4 Weeks | 2 | 2 |
| 8 Weeks | 2 | 0 |
| 12 Weeks | 2 | 0 |
| 16 Weeks | 2 | 0 |
| 16 Weeks | 2 | 0 |
| 21 Weeks | 2 | 0 |
| | SUBTOTAL N = 17 | SUBTOTAL N = 7 |
| ADULT CYCLOSPORINE TREATED RATS | | |
| 2 Weeks | 3 (sc = 1) | 3 (sc = 1) |
| 4 Weeks | 1 (sc) | 1 |
| 6 Weeks | 1 (sc) | 1 |
| 8 Weeks | 2 (sc = 1) | 1 (sc = 1) |
| 10 Weeks | 2 | 0 |

TABLE 1-continued

POST-TRANSPLANTATION SURVIVAL DATA
FOR GRAFTED NT2N CELLS

| Post-transplant survival | Number Of Rats injected w/NT2N Cells | Number Of Rats with viable NT2N cell grafts |
|---|---|---|
| 11 Weeks | 3 | 0 |
| 12 Weeks | 1 (sc) | 1 |
| | SUBTOTAL = 13 | SUBTOTAL = 7 |
| | GRAND TOTAL = 68 | GRAND TOTAL = 30 |

TABLE 2

POLYPEPTIDE AND CELL SPECIFICITY OF
ANTIBODIES AND THEIR
REACTIVITY WITH GRAFTED NT2N CELLS

| POLYPEPTIDE | ANTIBODY | DILUTION pg/ml | NT2N GRAFT |
|---|---|---|---|
| NEURONS | | | |
| Clathrin light chain | LCB2 | 0.1 | +/− |
| MAP2 | AP14 | 1:100 | + |
| MAP5 | AA6 | 1:1500 | + |
| NF-H, P$^{+++}$ | RMO24 | Neat | − |
| NF-H, P$^{+++}$ | RMO217 | Neat | − |
| NF-H, P$^{+}$ | TA51 | 1:20 | + |
| NF-H/M, P$^{-}$ | RMdO2O | 1:10 | + |
| NF-H, P$^{++}$ | HO14 | 1:25 | + |
| NF-M, p$^{ind}$ | RMO254 | 1:25 | + |
| NF-L, p$^{ind}$ | NR 4 | 1:10 | + |
| NF-L, p$^{ind}$ | Anti-NF-L | 1:50 | + |
| Neuron Specific Protein | NST11 | 1:10 | − |
| Protein Kinase Cy | PKC66 | Neat | − |
| Tau | T14 | Neat | + |
| Tau | 134 | 1:500 | +/− |
| Tau (fetal/PHF) | T3P | 1:50 | + |
| Tau (fetal/PHF) | PHF1 | 1:2000 | +/− |
| NEURONS AND NEUROENDOCRINE CELLS | | | |
| Chromogranin | LK2h10 | 1:500 | − |
| Synaptophysin | SY 38 | 1:100 | +/− |
| Tyrosine Hydroxlase | Anti-TH | 1:100 | − |
| NEUROEPITHELIAL STEM CELLS | | | |
| Nestin | Anti-Nestin | 1:2000 | − |
| GLIAL CELLS | | | |
| GFAP | 2.2B10 | 1:500 | − |
| MBP | Anti-MBP | 1:100 | − |
| NEURAL, MESENCHYMAL & OTHER CELLS | | | |
| N-CAM | MOC 1 | 1:10 | + |
| p75 NGFR | Me 20.4 | 1:100 | − |
| Vimentin | V9 | 1:100 | − |
| Macrophage marker | ED1 | 1:500 | − |

Example 3
Sensitivity of Dopaminergic Expression in NT2N neurons to Physical Damage:

In these experiments, the dopaminergic phenotype of NT2N neurons was investigated. Immunohistochemical analysis showed that NT2N neurons express robust levels of tyrosine hydroxylase (TH), the rate limiting enzyme in dopamine (DA) synthesis, during their differentiation but not after neuronal purification. TH expression increased during the five week retinoic acid differentiation period but was negligible after neuronal purification. Western blots and HPLC analysis confirmed the immunocytochemical data and demonstrated DNA (without noradrenalin or adrenalin) in NT2N cultures. Damage from mechanical manipulation was the causal factor in elimination of TH expression during the purification procedure. The decrease in dopaminergic phenotype was not due to transient expression as the neurons expressed TH indefinitely without mechanical disturbance. Mechanical damage did not cause significant reductions in neuronal numbers, indicating that these results do not merely reflect the death of dopaminergic neurons. After NT2N neuronal purification, TH expression was enhanced by the addition of a cocktail containing growth factors, second messenger system components, and dopamine. TH expression could also be slightly maintained through changes in the purification methods. The selective dopaminergic sensitivity to damage makes these cells attractive for investigating the regulation of TH and DA. Additionally, these neurons may be useful as a transplantation therapeutic in Parkinson's disease.

The following is a review of experiments performed to assess dopaminergic expression in NT2N neurons.
MATERIALS AND METHODS Purified NT2N neuronal cells were prepared from NT2 progenitor cells as described by Pleasure et al. 1992 *Journal of Neuroscience* 12(5):1802–15 and Kleppner et al. 1995 *Journal of Comparative Neurology* 357(4):618–32. NT2 precursor cells were split 1:8 (~2.3×10$^6$ cells per 75 cm$^2$ flask) into either a 75 cm$^2$ Corning flask, or onto glass coverslips in a 10 cm dish (for immunohistochemistry), and fed twice weekly with Dulbecco's modified Eagle's medium, high glucose (DMEM-HG; Gibco, Grand Island, N.Y.) with 10% fetal bovine serum (FBS; Hyclone, Logan, Utah), 1% Penicillin/Streptomycin (P/S; Biosciences, Lenexa, Kans.), and 10 μM retinoic acid (RA, Sigma, St. Louis, Mo.) for five weeks. Except as noted below, cells in 75 cm$^2$ flask were treated with versene (0.02% EDTA in HBSS) for 10 minutes, trypsin (0.5% trypsin, 0.53 mM EDTA-4Na, Gibco, Grand Island, N.Y.) for 2 minutes, triturated 30 times with a 5 ml pipette, split 1:6 into 225 cm$^2$ flasks, "R1", and fed twice a week for ten days with DMEM-HG, 5% FBS, 1% P/S with or without mitotic inhibitors (1 μM uridine, 1 μM FUDR, and 0.1 μM ARAC; Sigma, St. Louis, Mo.). At this point, a pure population, "R3", of NT2N neuronal cells was dislodged from the flasks by rinsing the cells with PB Hanks, treating the cells for 2.5 minutes with trypsin, and striking the flask sharply once on each side. DMEM (10 ml) with 10% FBS and 1% P/S was added, and the neurons were gently drawn up with a 10 ml pipette. Pure neurons were plated on poly-d-lysine (Sigma, St. Louis, Mo.) and MATRIGEL (Collaborative Research, Bedford, Mass.) coated coverslips, dishes or flasks.

Treated cells were fed twice a week with 10 ng/ml acidic fibroblast growth factor (aFGF; Promega, Madison, Wis.); 10 μM DA (Sigma, St. Louis, Mo.), 200 nm tumor promoting factor (tpa; Sigma, St. Louis, Mo.); 50 μM forskolin (Sigma, St. Louis, Mo.); and 250 μM IBMX (Sigma, St. Louis, Mo.).

PC12 cells were grown in Falcon flasks in RPMI 1640 with 10% heat-inactivated donor horse serum (DHS), 5% FBS, and 1% P/S; fed twice a week; and split 1:5 once a week in conditioned media (50% supernatant from the cells and 50% fresh media). For neuronal differentiation, 50–100 ng/ml NGF was added to the media three times a week for one week. NGF was extracted from mouse salivary glands in accordance with known procedures.
Immunohistochemistry:

Cells were rinsed with PBS (pH 7.3) and fixed with 4% paraformaldehyde for 10 minutes at room temperature. The coverslips were overlaid with primary antibodies in PBS with 0.2% Triton X-100 overnight at 4° C. The coverslips were washed with PBS and visualized with a peroxidase anti-peroxidase detection system with diaminobenzidine as the chromagen or with Texas Red (TXR) or fluorescein isothiocyanate (FITC)-coupled secondary antibodies (Jackson Immunoresearch, West Grove, Pa.); washed with PBS, and mounted with Fluoromount-G (Southern Biotechnology Associates, Inc., Birmingham, Ala.). The primary antibodies used were against: human specific neurofilament M (HO14,), MAP2 (AP14), TH (polyclonal obtained from Pel Freeze, Rogers, AR or Chemicon, Temecula, Calif.; monoclonal obtained from Boehringer Mannheim, Indianapolis, Ind.), GFAP (2.2B10) and glutamic acid decarboxylase (GAD-1).

Light microscopic immunohistochemical studies were conducted on paraffin sections. In these experiments, deparaffinized sections were incubated with the primary antibody overnight and the bound antibody was visualized using a peroxidase anti-peroxidase detection system with diaminobenzidine as the chromagen. All sections were counterstained with hematoxylin.

HPLC Analysis:

Cells were rinsed twice with ice cold PBS, scraped, and homogenized in 0.1 N $HClO_4$ with 1 mM EDTA, pH 5.7. Samples were sonicated for 10 seconds, and spun for 10 minutes at 10,000 rpm. Protein assays were performed and the remainder of the supernatant was frozen at −70° C. Samples were kept on ice during preparation for analysis and shipped frozen to Nichols Institute Diagnostics (San Juan Capistrano, Calif.) for HPLC analysis.

Western Blotting:

NT2 precursor cells, RA treated NT2N cells, pure NT2N neurons or NGF-treated PC12 cells were scraped with 250 μl of cell lysis buffer containing 50 mM Tris-HCl, 1% NP40, 5 mM EDTA, and 150 mM NaCl. The lysate was sonicated and centrifuged at 40,000× g for 30 minutes at 4° C. Protein concentration was determined with Coomassie Blue (Pierce, Rockford, Ill.), and 50, 25 or 10 μg of protein in sample buffer was loaded in each lane. Lysates were run on 7.5% SDS-PAGE gels, and transferred to nitrocellulose. Blots were blocked with 5% milk for 30 minutes, then probed with primary antibody diluted in the blocking solution; rabbit anti-TH (Pel Freeze), rabbit anti-TH (Chemicon), mouse anti-TH (Boehringer Mannheim). The blots were incubated on a rotating table overnight at room temperature, then rinsed three times for 10 minutes with TTBS. Secondary antibody was diluted in blocking solution, and added for one hour at room temperature. Blots were then rinsed as above. The immunobands were detected with peroxidase antiperoxidase or avidin biotin complex detection system with diaminobenzidine as the chromagen.

Implantation:

Homozygous athymic (nu/nu) mice were obtained from the National Cancer Institute. Females (21–24 days old) were anesthetized intraperitoneally with 175 mg/kg Ketamine and 15 mg/kg Xylazine. Sterile pulled glass pipettes attached to a syringe pump were used for the implantation. The needle tip was broken off to a bore size that would just draw up fluid and was positioned using a stereotactic manipulator. The implantation procedure was performed under a dissecting microscope. An incision was made in the skin and a hole was made in the dura at the implantation site. Cells were implanted into the right striatum. A NT2N cell suspension (1–2 μl) was injected at a rate of 0.2–0.4 μl/minute followed by a 0–5 minute wait interval and slow retraction of the needle. The skin was closed with a wound clip. No behavioral effects were observed at any time after the surgery.

Tissue Processing:

Animals were euthanized by transcardiac perfusion under deep anesthesia induced with Ketamine/Xylazine. The animals were perfused initially with 0.1 M PBS, pH 7.4, followed by either 4% paraformaldehyde (pH 7.4) or 70% ethanol in isotonic saline (150 mM NaCl), pH 7.4. The brains were removed immediately and post-fixed (10 minutes with paraformaldehyde followed by overnight washing with PBS or overnight with buffered ethanol). The brains were then infiltrated and embedded in paraffin. Near serial 6 μm thick sections were cut on a rotary microtome, collected on APES coated slides and processed for immunohistochemistry.

RESULTS

NT2N Neurons Contain TH And Dopamine During RA Differentiation:

TH expression was visible after the first week of RA treatment in NT2N neurons. The number of TH-expressing cells increased as the number of neurons increased (assessed by HO14 immunoreactivity). The majority of the neuronal cells in the cultures expressed abundant TH throughout the five week differentiation period. Immunofluorescence data was confirmed using two commercially available TH antibodies. Western blots with the three TH antibodies confirmed the immunocytochemical results. Prominent bands at 61,300 Da, appropriate for TH, were seen in PC12 cells, with no TH bands in NT2 precursor cells, moderate bands in non-dissociated NT2 RA treated cells, and faint bands in purified NT2N neuronal cells.

HPLC analysis showed that five week RA treated NT2 cells contained 11.9 pg/mg (78 pmol/g) of dopamine. NT2 precursor cells did not contain detectable levels of dopamine, while purified NT2N neurons contained barely detectable levels. Control protein from NGF treated PC12 cells contained >350 pg/mg proteins. Neither noradrenalin nor adrenalin were found in any of the samples. As the HPLC DA data directly correlates with TH expression assessed by both immunohistochemistry and Western blotting, TH immunoreactivity appears to be a valid approximation of dopaminergic phenotype.

TH Expression Is Lost Through Mechanical Manipulation:

TH expressing NT2N neurons are not simply killed during the neuronal purification procedure. Large numbers of purified neurons are harvested from cultures where the majority of neurons expressed TH before purification. If the TH expressing neurons were dying, few purified neurons would be obtained. Since purified NT2N neurons contain very low levels of TH and DA, some element of the purification procedure must cause the decrease. Each component in the purification procedure, from differentiation to R3 was assessed for effect on TH expression. The tested elements included chemical dissociation (versene and/or trypsin), mechanical dissociation (trituration), plotting density, length of time in culture, treatment with mitotic inhibitors, or the presence of NT2 non-neuronal cells. The only influence on TH expression was observed with mechanical dissociation of the cultures. Standard trituration decreased TH expression, while gentler or less trituration led to a corresponding increase in TH expression. The amount of trituration needed to obtain pure, dissociated, NT2N neuronal cultures yielded very low TH immunoreactivity. The presence of non-neuronal cells did not maintain TH expression, and the expression was not down-regulated with either increased time in culture or the presence of mitotic inhibitors. TH is not expressed transiently during the maturation of these neurons, since increased time in culture had no effect on TH levels. TH expression was also unaffected by versene, trypsin or cell density. The change in TH expression is not reflected by changes in the expression of glutamic acid decarboxylase (GAD), the rate limiting enzyme in GABA synthesis, which was found ubiquitously in NT2N neurons both at the R1 stage and at the R3 stage.
TH Expression Can Be Enhanced In Purified NT2N:

It was also found that a cocktail of growth factors, second messenger system components, and dopamine (aFGF, DA, tpa, forskolin, and IBMX) could affect TH expression in NT2N neurons, both as purified neurons and at earlier times. When applied immediately after either R3 or R1 replating, the TH expression of the NT2N neurons increased. Application of these factors after both R1 and R3 replating increased TH expression, but did not increase TH expression to levels higher than those found with factor application after R3 replating alone. When factors were given during the differentiation of the NT2N neurons, the number of neurons obtained was greatly reduced, presumably because the toxicity of these factors.

Throughout RA treatment and again during the ten days of R1, the NT2N neurons extend processes which are broken off during replating. Since the decrease in TH expression is caused by mechanical disruption, purification of the NT2N neurons while they had shorter neurites was examined. The length of RA treatment was varied from 3, 4 or 5 weeks and the length of R1 was varied from 4 to 10 days. Neurons were also plated onto a monolayer of feeder cells (non-neuronal NT2 cells or primary astrocytes) at R1 replating.

Increases in TH expression were seen when the RA-treated NT2 cells were plated directly onto feeder layers during R1 and when R1 times were decreased to four days. R3 replating after four days of R1 on any of the feeder monolayers produced the highest TH expression, but many non-neuronal cells were carried through the R3 replating procedure. The tightly bound non-neuronal cells that are carried through to R3 may physically protect the neurites from damage or the feeder cells may provide trophic support. Although plating NT2N cells onto non-neuronal cells at the R3 replating did not affect TH expression, slight increases in TH were seen when cells were plated onto monolayers at the R1 replating. This also suggests a trophic role for the feeder cells. The lack of increased TH expression when NT2N neurons are plated onto feeder cells at the R3 replating may reflect a TH level that is too low by this point to be recovered by the trophic support of the feeder cells. Decreasing the length of RA treatment did not affect the loss of TH expression during replating. None of the other manipulations described produced any changes in TH expression.

Since TH expression was partially maintained by plating the RA treated NT2N cells onto astrocytes at the R1 replating, the effect of plating traditionally purified R3 neurons onto cortical or striatal primary astrocytes on the TH phenotype of these cells was examined. Although this manipulation did not increase the number of TH expressing neurons, a similar percentage of neurons that were TH immunoreactive at the time of their plating (<5%) robustly expressed TH after seven months in co-culture. This also indicates that increased time in culture is not responsible for the observed decreases in TH expression, again ruling out the possibility of transient, maturationally controlled, TH expression.
NT2N Neurons Grafted Into Murine Striatum Do Not Robustly Maintain Their TH Phenotype:

Since murine striatum had been shown to induce some implanted NT2 precursor cells to differentiate into TH expressing neurons, the ability of this milieu to help to retain TH expression in non-replated, RA treated NT2N cells was examined. Cells were implanted into murine striatum after one, three or five weeks of RA treatment. Post-implantation survival times ranged from one to four weeks, and TH was assessed by immunohistochemistry. Endogenous substantia nigra was used as a positive control. Cells implanted after one or three weeks of RA treatment showed faint TH immunoreactivity within the graft areas at survival times up to four weeks. NT2N cells treated with RA for five weeks and implanted into the striatum were not immunoreactive within the graft, but occasional strong immunoreactive single cells were found adjacent to the graft within the host striatal tissue.

DISCUSSION

As shown herein, most NT2N neurons contain TH and DA when differentiated and it is the mechanical manipulation of these cells in traditional purification procedures which decreased or eliminated this phenotype. As also shown herein, changes in the neuronal purification procedure or addition of a cocktail of factors can result in an increase in TH expression. While this increase is slight, the functional recovery seen in the NT2N implants, despite the low numbers of dopaminergic cells, indicates that just a small number of DA neurons in a transplant can provide therapeutic benefit. Thus, the rescue or induction of TH seen with manipulations described herein could provide viable, reproducible cultures which contain enough dopaminergic neurons for functional improvement following implantation into Parkinson's Disease patients.

Example 4

Adaptation of Grafted Neuronal Cells in Undamaged Spinal Cord:

Engraftment properties of pure, post-mitotic human neurons (NT2N neurons) in the spinal cord were investigated in mice. The age of the host at implantation (neonate, young adult, adult), spinal cord locations (dorsal, central, ventral), and post-implantation survival time (up to 15 months) were varied. Maturation, phenotypic stability, neurite outgrowth patterns and integration with host tissue (myelination, destination, connectivity) were assessed. It was found that grafted NT2N cells acquired fully mature stable neuronal phenotypes; their neurite outgrowth mirrored that of the surrounding host processes in both gray and white matter; their processes were myelinated by the host, extended for distances >2 cm, and grew within spinal nerves. After traveling in spinal cord white matter tracts, NT2N processes turned to gray matter, where they exhibited synaptophysin immunoreactivity consistent with graft to host synaptic contacts. Thus, it appears that graft integration with host tissue is not dependent on neuronal progenitor cells nor on the presence of transplanted non-neuronal cells. The phenotypic stability and lack of migration of the immature but post-mitotic neurons also suggests that host influence on the phenotype of grafted cells is limited either to dividing cells or to neurons which are able to migrate into host parenchyma. The ability of the grafted human NT2N cells to integrate into the spinal cord in a location dependent manner, while maintaining a stable intrinsic neuronal phenotype is indicative of these cells being useful in transplantation therapeutics.

The following is a review of experiments performed to characterize the properties of NT2N cells following transplantation into spinal cords of mice.

MATERIALS AND METHODS

NT2N neurons were generated from the parent NT2 cells as described previously by Pleasure et al. 1992 *Journal of Neuroscience* 12(5):1802–15 and Kleppner et al. 1995 *Jour-* nal of Comparative Neurology 357(4):618–32, with the following modifications. Cells were split 1:8 to a T75 flask and fed twice weekly with Dulbecco's modified Eagle's medium, high glucose (DMEM-HG; Gibco, Grand Island, N.Y.) with 10% fetal bovine serum (FBS; Hyclone, Logan, Utah), 1% penicillin/streptomycin (P/S; Biosciences, Lenexa, Kans.), and 10 $\mu$M retinoic acid (RA; Sigma, St. Louis, Mo.) for five weeks. Cells were then split 1:6 into two T225 flasks and fed twice a week for ten days with DMEM-HG, 5% FBS, 1% P/S, and mitotic inhibitors (1 $\mu$M uridine, 1 $\mu$M FUDR and 0.1 $\mu$M ARAC; Sigma, St. Louis, Mo.). At this point, a pure population of NT2N cells was dislodged from the flasks. The NT2N neurons were rinsed, resuspended in serum-free DMEM-HG and triturated to a single cell suspension for injection at densities of approximately 10,000–40,000 cells/$\mu$l. The NT2N cells were maintained on ice prior to implantation. Cell viability was 80–100% at the start of the implantation session and 60–80% at the termination of a typical 3–4 hour implantation session. However, if cells were plated after four hours on ice, only 30–50% of the cells adhered. Thus, animals injected at the end of a surgery session received fewer viable NT2N neurons than those injected early in the session (four animals were injected per session).

Implantation:

Homozygous athymic (nu/nu) mice were obtained from the National Cancer Institute. To study NT2N neurons grafted into the spinal cord of juvenile animals, 21–24 day old females were anesthetized intraperitoneally with 175 mg/kg Ketamine and 15 mg/kg Xylazine. Adult mice were anesthetized with 130 mg/kg Ketamine and 30 mg/kg Xylazine. Juvenile and adult animals were immobilized in a sling to minimize the effects of breathing during the procedure. Neonatal mice were generated by breeding heterozygous females (Charles River, Wilmington, Mass.) to homozygous male nude mice. Neonates were anesthetized by hypothermia in an ice water slurry and maintained on a cold plate during the implantation procedure, after which they were revived by slow warming to 37° C.

Figure 4:
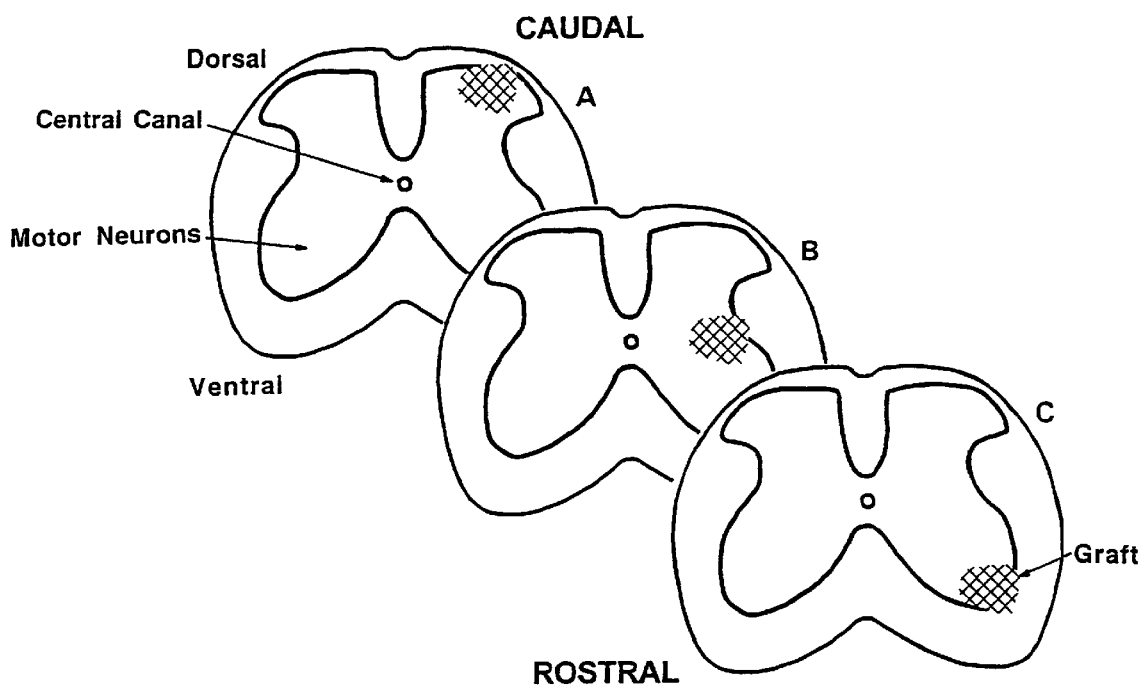
FIG. 4 is a schematic showing the locations of neuronal cell implantations in spinal cords of mice. NT2N neurons were implanted at a 45–50° angle from vertical, in continuous grafts from ventral to dorsal gray matter. Grafts were either located along the lateral gray/white matter interface as depicted herein, or close to the midline of the cord. In more caudal positions, the graft is located dorsally (A), in more rostral locations, it is central (B) and at the farthest rostral locations, it is ventral (C).

Sterile pulled glass pipettes attached to a syringe pump were used for implantation. The needle tip was broken off to a bore size that would just draw up fluid and was positioned using a stereotactic manipulator. The implantation procedure was performed under a dissecting microscope. The fascia and muscle were not removed, but were incised to facilitate dissection of the dorsal lamina which were detached on three sides and lifted rostrally, exposing the cord. A small hole was made in the dura at the implantation site. NT2N neurons were implanted into the right side of the spinal cord, between T13 and L1 at a 45–50° angle to the cord surface, an angle that optimized later morphological assessment of the transplanted neurons. Implants were directed parallel to, and either 0.1 mm or 0.6 mm lateral to, the midline. NT2N neurons were implanted from the ventral horn through central and dorsal areas (FIG. 4). One to two $\mu$l of an NT2N cell suspension was injected at a rate of 0.2–0.4 $\mu$l/minutes followed by a 0–5 minute wait interval and slow retraction of the needle. The bone flap was replaced, fascia and muscle re-apposed, and the skin closed with wound clips or sutures. No behavioral abnormalities were observed at any time after surgery.

Tissue Processing:

Animals were euthanized by transcardiac perfusion under deep anesthesia induced by Ketamine/Xylazine. The animals were perfused initially with 0.1 M PBS, pH 7.4, followed by either 4% paraformaldehyde (pH 7.4) or 70% ethanol in isotonic saline (150 mM NaCl), pH 7.4. Spinal cords were either removed immediately and post-fixed (overnight with buffered ethanol or 10 minutes with paraformaldehyde), or the spinal column was removed and post-fixed overnight before cord removal. The cords were then infiltrated and embedded in paraffin as described by Trojanowski et al. 1989 Journal of Neuroscience Methods 29(2):171–80. The infiltrated cords were either blocked into 4–7 segments for coronal sectioning and embedded in paraffin or they were embedded whole for longitudinal section. Near serial 6 $\mu$m thick sections were cut, collected on poly-1-lysine or APES coated slides and processed for immunohistochemistry.

Immunohistochemistry:

The methods used for the light and confocal microscopic immunohistochemical studies conducted on paraffin sections were performed in accordance with procedures described by Lee et al. 1987 Journal of Neuroscience 7(11):3474–88 and Trojanowski et al. 1989 Journal of Neuroscience Methods 29(2):171–80. Deparaffinized sections were incubated in the primary antibody overnight at 4° C., and the bound antibody was visualized using either peroxidase anti-peroxidase reactions with diaminobenzidine (DAB) as the chromagen or fluorescent probes (FITC or Texas Red, Jackson Immunoresearch, West Grove, Pa.). DAB sections were counterstained with hematoxylin. The properties of the primary antibodies are summarized below. They included three monoclonal antibodies (Mabs) that recognize human-specific epitopes in neuronal proteins expressed by the NT2N neurons. These Mabs (MOC-1, hSYN, and HO14) enabled unequivocal detection of the grafts as described by Tonder et al. 1988 Experimental Brain Research 72(3):577–83, Trojanowski et al. 1993 Experimental Neurology 122(2):283–94 and Kleppner et al. 1995 Journal of Comparative Neurology 357(4):618–32. Confocal microscopy was performed on sections visualized with fluorescent secondary antibodies.

Analysis

Eighty-six mice with spinal cord grafts were analyzed. Numbers of animals in each groups were as follows:

Survival post-implantation

| 1–2 weeks | 1 mo. | 2 mos. | 3 mos. | 4 mos. | 5 mos. | 6 mos. | 7–8 mos. | 15 mos. |
|---|---|---|---|---|---|---|---|---|
| 20 | 18 | 17 | 6 | 5 | 7 | 4 | 4 | 4 |

| Graft Placement | | | | Age at implantation | |
|---|---|---|---|---|---|
| Midline | 19 | Dorsal | 5 | neonate | 8 |
| | | Central | 12 | 21–27 days | 73 |
| | | Ventral | 15 | adult | 5 |
| Lateral | 67 | Dorsal | 53 | | |
| | | Central | 63 | | |
| | | Ventral | 61 | | |

One case was analyzed directly after surgery (survival time=0). Medial grafts were located near the midline of the spinal cord; lateral grafts were located near the gray/white matter border. Neonates were 1–2 days old and adults were up to 85 days old. The majority of animals were implanted when 24 to 25 days old. All cases that had grafts located along the gray/white matter interface that had no background and were fixed in ethanols, were further analyzed for long distance outgrowth (26 animals).

Graft size was approximated for every case using NIH Image software to outline the grafts in every 20th and 30th anti-human NCAM (MOC-1) immunostained section at low magnification, and extrapolating to estimate total volume.

Cell size and shape were similarly assessed in a subset of cases by measuring the largest and most clearly defined cell bodies in sections immunostained with MOC-1 or HO14. Long, thin, non-tapering processes were classified as axonal while thicker, tapered processes were judged to be dendritic. Sample sections were immunostained with antibodies specific for axonal or dendritic proteins for confirmation (HO14, M13). Measurements of maximal axonal outgrowth were made on each section immunostained for human NCAM or human NFM (every 20th or 30th section). The distance to the nearest edge of the graft from the end of the longest clearly immunoreactive fiber in both rostral and caudal directions was measured. Measurements were corrected for tissue shrinkage during processing.

RESULTS

Implanted NT2N Neurons Maintain A Stable Neuronal Phenotype And Mature In Situ:

Human-specific MOC-1 Mab located grafted human neurons and delineated the graft site in situ. The tightly clustered NT2N neuronal perikarya visible in hematoxylin-stained sections demarcated the implant, confirming MOC-1 results. The sizes of the grafts ranged from $0.036 \times 10^{-3}/mm^3$ to $0.254/mm^3$. This variability did not reflect the survival time or the age of the host at implantation. There was no evidence of graft rejection or tumorigenicity.

In vitro, at the time of implantation, NT2N neurons expressed NCAM and GAD and low levels of synaptophysin, a developmentally regulated synaptic vesicle protein that indicates the present of synapse formations and synaptic activity. They did not express the adult neuronal markers tau or $P^{+++}NFH$. Similar immunoreactivity is seen after short survival time in vivo. With increasing time in situ, the grafted cells began to express $P^{+++}NFH$ and the adult tau isoform; by seven months post-implantation, the levels were indistinguishable from the host expression. Synaptophysin immunoreactivity also increased within the grafts; the graft/host interface was the last area to express synaptophysin in a pattern indistinguishable from the surrounding host tissue. GAD expression remained stable in all grafts at all post-implantation times. Tyrosine hydroxylase expression was negative in all cases. Neither the graft site nor host age at implantation affected the phenotype or morphology of implanted NT2N neurons.

Somal Morphology Remains Stable While Process Outgrowth Is Determined by the Host:

NT2N spinal cord grafts showed abundant neurite outgrowth into host parenchyma which was independent of the age of the host at implantation. This process outgrowth was location dependent, mirroring the patterns in the surrounding host tissue. Thin axon-like NT2N processes traveled with host axons, while thicker dendrite-like processes were randomly arrayed in the host gray matter near the graft. Graft processes were so closely apposed to host axonal bundles that the host bundles were often outlined by NT2N process immunoreactivity. Most NT2N axonal processes traveled with the large white matter tracts of the spinal cord (dorsal and ventral columns), especially where grafts were located near gray/white interfaces. Graft neurites also traveled long distances along longitudinal axonal bundles in the gray matter and frequently crossed the spinal cord midline in gray matter where host fibers cross. No evidence of NT2N fibers fasiculating with themselves was seen.

The majority of grafts had no solitary NT2N neuronal perikarya within host tissue, showing that grafted NT2N somas did not migrate away from the injection site. The farthest a NT2N soma was found in the body from the graft was approximately 200 $\mu$m from the graft in this plane. This is the upper limit of the actual distance of these cells from the graft, as the graft is also directly above these cells in the dorsal/ventral plane, due to the angle of the implantation.

Implanted NT2N cell bodies were measured and compared to each other by their location within the host. They were also compared to host spinal cord motor neurons and to host dorsal horn neurons. Immediately after implantation, the grafted cells had a uniform size and shape and were within the needle track. By two weeks post-implantation, the needle track was no longer clearly defined and the NT2N neuronal cell somas had a slightly more varied appearance. However, regardless of the density or position of cells in the graft, the CNS implantation site, or the age of the host at the time of implantation, the cell soma size distributions of the NT2N neurons remained the same, i.e. approximately ⅓ the size of murine motor neurons and ¾ the size of host dorsal spinal cord neurons.

NT2N Processes Travel Long Distances in the Spinal Cord:

The robust outgrowth produced by the grafted neurons extended over long distances in the host. For example, HO14 immunoreactive graft fibers traveled along host white matter bundles and in lateral white matter over 1 cm away from the graft border.

NT2N neurons implanted at neonatal, juvenile and adult ages all showed similar axonal outgrowth. Thus, representative juvenile implantation cases in which the grafts were located within the gray matter near the white matter border are presented in detail here. Long distance outgrowth was assessed by measuring the longest unequivocally immunoreactive process in each section. Single graft fibers grew along host fibers, similar to the axons of embryonic human or murine cells implanted into rat spinal cords as described by Wictorin and Bjorklund, 1992 *Neuroreport* 3(12):1045–8 and Li and Raisman, 1993 *Brain Research* 629(1):115–27. When outgrowth was assessed with MOC-1, distal immunoreactivity decreased at post-implantation over 6 weeks. When assessed with HO14, however, distal immunoreactivity did not decrease over time. The rate of maximal outgrowth seen with HO14 immunoreactivity was ~1.4 mm/week for the first six weeks, followed by a rate of at least 1 mm/month thereafter. NT2N neurites grew for distances over 2 cm, continuing beyond the analyzed spinal cord segments (approximately C4-S1). Outgrowth was equal in rostral and caudal directions, with no preference for dorsal or ventral tracts.

NT2N Neurons Are Specifically and Full Integrated into the Host Spinal Cord:

Myelination was examined using confocal double-immunofluorescence with an anti-myelin-associated glycoprotein antibody (MAG) and HO14 (to identify NT2N processes). Some, but not all grafted processes were myelinated within the graft. The close proximity of myelinated host fibers to NT2N processes in host white matter tracts precluded definitive assessment of the myelination state of NT2N fibers within the tracts.

Long-distance grafted neuronal processes took different routes after traveling for some distance within white matter tracts. Axons continued within the white matter tracts, crossed into the peripheral nervous system (PNS) to travel within spinal roots, or turned back into gray matter. Many dendrite-like processes were found immediately adjacent to the grafts, while large numbers of axon-like processes traveled along endogenous white matter tracts or bundles. Many long-distance processes continued traveling along the matter tracts beyond the analyzed segment. In 3 of the 15 month post-implantation cases and in 1 of the 7 month post-implantation cases, NT2N axonal processes were also found within spinal nerves. Although not all spinal nerves were examined, NT2N processes were not seen in spinal roots after shorter survival times, and the number of NT2N processes found within spinal roots was low.

Another axonal course initially followed the large white matter tracts but abruptly turned, exited the host tract and re-entered gray matter. Many NT2N processes followed this route and appeared to terminate within the gray matter. To determine if these processes elaborated into terminal arborizations and synapsed with host cells, a human specific anti-synaptophysin antibody (hSYN) was used. Punctate immunoreactivity was observed near HO14 immunoreactive processes in host gray matter. In graft areas, confocal double immunofluorescence studies with hSYN and HO14 showed robust punctate hSYN immunoreactivity within the grafts and in the surrounding host spinal cord. A single HO14-negative neuronal shape (host neuron or non-reactive grafted soma) is highlighted by punctate hSYN immunoreactivity just outside the graft. Confocal double immunofluorescence studies in host areas devoid of grafted cell bodies or dendritic processes also showed punctate hSYN immunoreactivity near HO14 immunoreactive processes, which is indicative of graft to host synaptic connections in the gray matter.

DISCUSSION

This study demonstrates that implanted human clonal neurons can full integrate into spinal cord. NT2N neurons engraft stably into the murine spinal cord, exhibit a mature neuronal phenotype regardless of local environment, and do not show any obvious changes in phenotype with respect to the in situ location or the age of the host at implantation. Local and long distance process outgrowth follows the host anatomic patterns and fiber tracts, and NT2N processes are myelinated by the host and grow into spinal nerves. Additionally, neurite morphology and synaptophysin expression suggest synaptic contacts between graft and host cells. This model is thus useful in the development of strategies for the treatment of spinal cord injuries and to further investigate the neurobiology of human neuronal transplants.

Example 5

Formation of Functional Synapses between Human NT2N Neurons Grown on Astrocytes:

The formation of functional synapses is a late milestone of neuronal differentiation. The establishment of functional synapses can be used to assess neuronal cell lines. In these experiments, the in vitro conditions that influence the ability of human neurons derived from the NT2 cell line (NT2N neurons) to establish synapses was examined. The morphologic, immunologic and electrophysiologic characteristics of these synapses was examined. In the absence of astrocytes, NT2N neurons rarely formed synapses and their action potentials were weak and uncommon. In contrast, when plated on primary astrocytes, NT2N neurons were able to form both glutamatergic excitatory (71%) and GABAergic inhibitory (29%) functional synapses whose properties (kinetics, ion selectivity, pharmacology, and ultrastructure) were similar to synapses of neurons in primary culture. Additionally, co-culture of NT2N neurons with astrocytes modified the morphology of the neurons and extended their in vitro viability to more than one year. Since astrocyte-conditioned medium did not produce these effects, it is believed that direct contact between NT2N neurons and astrocytes is required. Thus, it appears that NT2N neurons are similar to primary neurons in their synaptogenesis and their requirements for glial support for optimal survival and maturation.

The following is a review of experiments performed to assess functional synapses formed between NT2N neurons grown on astrocytes.

MATERIALS AND METHODS

NT2N neurons were generated from NT2 cells as described by Pleasure et al. 1992 *Journal of Neuroscience* 12(5):1802–15 and Kleppner et al. 1995 *Journal of Comparative Neurology* 357(4):618–32. Pure NT2N neurons were frozen and stored at −80° C. in 95% FBS with 5% DMSO. The age of NT2N neurons in this study refers to time in vitro after retrieval from the frozen state. For cultures of pure NT2N neurons, approximately $10^5$ freshly thawed NT2N neurons were plated on poly-d-lysine and MATRIGEL (Collaborative Research, Bedford, Mass.) coated 35 mm dishes. For co-culture, astrocytes were dissociated from the cerebral hemispheres of E18–21 rats (18–21 day gestation rats were obtained by dissection following $CO_2$ narcosis followed by rapid decapitation of the dam), maintained in MEM with 10% horse serum and allowed to proliferate in flasks until confluent (about two weeks). The confluent astrocytes were then treated with trypsin, triturated, and replated in 35 mm dishes. Astrocyte identification was confirmed by the characteristic "pavement" appearance of the monolayer under phase-contrast optics and by the expression of glial fibrillary acidic protein. After the replated astrocytes reached confluence again, approximately $10^5$ NT2N neurons were plated onto each 35 mm dish and maintained in DMEM-HG with 10% FBS. Mitotic inhibitors and antibiotics were generally not included in the medium. Astrocyte conditioned media was collected from 75 $cm^2$ flasks of confluent astrocytes after three days in culture and combined with freshly prepared media at a 1:1 ratio. "Banker" co-cultures of NT2N neurons with astrocytes, which permit co-culture but not contact, were prepared by plating pure NT2N neurons on coverslips treated with poly-d-lysine and MATRIGEL. These coverslips are set face down with 3 wax drops preventing contact with monolayers of confluent astrocytes grown in wells.

Immunohistochemistry:

For detection of synapsin I, cells were washed with PBS (pH 7.4) and fixed with 4% paraformaldehyde for ten minutes at room temperature. The coverslips were overlaid with primary antibodies against human-specific mid-size neurofilament subunit (hNFM), HO14 and synapsin I (Molecular Probes, Eugene, Oreg.) in PBS with 0.2% Triton X-100 overnight at 4° C. The coverslips were washed three times with PBS over one hour, then overlaid with Texas Red (TXR) and FITC coupled secondary antibodies (Jackson Immunoresearch, West Grove, Pa.) for one hour at room temperature, washed three times in PBS over one hour and mounted. The double labeled cultures were examined using a confocal microscope.

Electron Microscopy:

Cells were washed with PBS for two hours at 4° C. before fixation with 2% glutaraldehyde in PBS overnight (4° C.). The cells were then washed three times with 0.1 M sodium cacodylate and osmicated with 2% osmium in 0.1 M sodium cacodylate for 60 minutes (4° C.). Cells were then washed twice with 0.1 M sodium cacodylate, twice with deionized $H_2O$, stained enbloc for 30 minutes with 2% aqueous uranyl acetate, rinsed with $dH_2O$ (4° C.) and dehydrated in ethanol (EtOH). Cultures were then incubated in 1:1 ratio of EtOH:propylene oxide for 5 minutes and twice in absolute propylene oxide (5 minutes each) before infiltration with 1:1 ratio of propylene oxide:EPON 812 for two hours followed by 100% EPON for one hour. The cells were left in a fresh change of EPON overnight in a vacuum desiccator (4° C.).

The next day, the beem capsule was filled and the resin was partially cured at 70° C. The cultures were then inverted onto the resin, secured, aligned, cured at 70° C. for 48 hours, cooled and cut. EM analysis allowed the identification of synaptic ultrastructure.

Electrophysiology:

For electrical recording, growth medium was replaced with an extracellular recording solution containing 140 mM NaCl, 3 mM KCl, 2 mM $MgCl_2$, 2 mM $CaCl_2$ and 10 mM HEPES, pH 7.3. For voltage-clamp recordings, KCl in the internal solution was replaced by 130 mM CsGluconate and 10 mM CsCl. Borosilicate glass pipettes (WPI) were pulled to a resistance of 5–10 MΩ. For paired recordings, an Axoclamp-2A patch-clamp amplifier was used. For single cell recordings, a Dagan 3900 integrating amplifier was used. Data were filtered at 1 kHz, sampled at 2 kHz, and stored on disk using pClamp6 (Axon Instruments).

RESULTS

Astrocytes Influence NT2N Neuronal Morphology:

NT2N neurons co-cultured with primary astrocytes underwent morphological, biochemical, and physiological transformations compared with control cultures of NT2N neurons grown in the absence of astrocytes. For example, immediately after plating the NT2N neurons onto primary astrocytes, the NT2N neurons rapidly spread out on top of the astrocytic monolayer rather than forming the tight clusters of cell bodies characteristic of pure NT2N neuronal cultures. This suggests that NT2N neurons have a higher affinity for astrocytes than for themselves. Further, changes in morphology of NT2N neurons in astrocyte co-culture allowed paired recordings, which are technically difficult to obtain from NT2N neurons in dense clusters.

A second consequence of astrocyte co-culture was an increase in the survival time of NT2N neurons. Previous studies have shown no NT2N neurons in pure culture to survive for longer than three months in vitro, whereas NT2N neurons co-cultured on astrocytes remain viable in culture for more than one year. To assess whether or not substances secreted by astrocytes mediate these effects, astrocyte conditioned medium was added to pure cultures of NT2N neurons or non-contacting "Banker" co-cultures of astrocytes and NT2N neurons were grown. Changes in morphology or increase in survival were not observed in either case, indicating that the effects of astrocytes on NT2N cells are not mediated solely by diffusible factors.

A third consequence of astrocyte co-culture was a change in the intrinsic electrical excitability of NT2N neurons. Although NT2N neurons were able to generate action potentials in the absence of astrocytes, their action potentials were of low amplitude and long duration. In contrast, NT2N neurons co-cultured with astrocytes generated action potentials with amplitudes of up to 50 mV and durations of less than 5 milliseconds, suggesting an increased density of sodium channels. Prominent after-hyperpolarizations were also observed in NT2N neurons co-cultured on astrocytes but not when NT2N neurons were cultured alone, indicating an increase density of potassium channels in the NT2N neurons in the presence of astrocytes.

Astrocyte Co-culture Affects Synaptogenesis In NT2N Neurons:

Immunohistochemical studies and electron microscopy (EM) provided structural evidence of synaptogenesis in the presence of astrocytes. When NT2N neurons were cultured on astrocytes, intense punctate immunoreactivity for synapsin I, a presynaptic vesicle-associated actin binding protein that is almost exclusively localized to the synapse, was seen along processes and often concentrated in proximal dendrites. In contrast, NT2N neurons in pure culture had more diffuse and less intense immunoreactivity. This difference is believed to reflect both a smaller number of synaptic release sites and fewer vesicles per site. The formation of presynaptic specializations was detected by antibodies directed against the synaptic proteins synatophysin and synaptobrevin.

Ultrastructural details of synapses in pure NT2N cultures revealed rare, poorly formed synaptic profiles containing few vesicles, while abundant synaptic profiles were found in co-cultures of NT2N neurons and astrocytes. After co-culture, the NT2N synapses showed a thickening of closely apposed membranes with desmosome-like structure as well as a large number of tightly packed synaptic vesicles. The vesicles were predominantly small, clear and spherical, ranging in size from 34 to 67 nm. A few large dense core vesicles and large clear vesicles were also observed near some synapses.

NT2N Neurons Form Functional Synapses In Co-culture:

The detection of spontaneous miniature excitatory and inhibitory synaptic currents (mEPSCs and mIPSCs) in NT2N neurons cultured on astrocytes is indicative of functional synaptic transmissions between NT2N neurons. mEPSCs and mIPSCs are believed to represent the release of individual quanta of neurotransmitter. The mean amplitude of mEPSCs detected in NT2N neurons was 23±13 pA (mean±S.D., n=7), which is similar to mEPSCs recorded from cultured primary neurons. Further, with a cell voltage-clamped at −40 mV, both excitatory and inhibitory inputs were detected, as inward and outward currents, respectively. Thus, single NT2N neurons can receive both excitatory and inhibitory inputs.

The presence and characterization of functional synapses between NT2N neurons were investigated by simultaneous electrical stimulation and recording from pairs of NT2N neurons. The criteria set for synaptic transmission were that the postsynaptic signal had: (1) an amplitude above the background noise, (2) a time course consistent with synaptic transmission (e.g. rapid onset and a slower exponential decay), (3) a constant latency with respect to the presynaptic action potential, (4) a consistent reversal potential, and (5) sensitivity to standard pharmacological agents. Whole cell patch-clamp recordings were established on pairs of NT2N neurons that were within 200 μm of each other. Depolarizing currents were injected into a current-claimed presynaptic NT2N neuron to elicit single action potentials while membrane current was recorded from a voltage-clamped postsynaptic cell. Synaptic activity between NT2N neurons was first detected after one month of co-culture with primary astrocytes. Fifty-six of 323 pairs of NT2N neurons co-cultured for longer than one month showed clear evidence of evoked postsynaptic currents, meeting all the criteria for synaptic transmissions. Recordings from synaptically connected pairs of cells showed that the postsynaptic currents were synchronized with the presynaptic action potential and clearly distinct from the background noise.

NT2N Neurons Utilize Glutamatergic Transmission:

The transmitter utilized between each pair of cells could be determined based on the ion selectivity, gating kinetics, and pharmacologic sensitivities of the postsynaptic receptors. Glutamatergic synaptic currents are mediated by cation selective channels with a reversal potential close to 0 mV. Application of 6-cyano-7-nitroquinoxaline-2,3-dione (CNQX), an AMPA GluR antagonist, selectively and reversibly eliminated the fast current component. Application of 2-amino-5-phosphonovaleric acid (APV), a selective NMDA GluR antagonist, reversibly and selectively eliminated the slow current component. The electrophysiological and pharmacological characteristics of these signals are indicative of presynaptic release of glutamate and postsynaptic activation of AMPA and NMDA GluR channels. Forty of the 56 synaptically connect pairs of NT2N neurons shared these characteristics, suggesting that a majority of synapses between NT2N neurons utilize glutamate as their neurotransmitter.

NT2N Neurons Also Use GABAergic Transmission:

In the remaining 16 pairs of synaptically connected NT2N neurons studied, the postsynaptic currents reversed between −60 and −70 mV, which suggested that they were inhibitory synaptic signals mediated by chloride channels. The average 10–90% rise time of the inhibitory currents was 2.6 milliseconds, with a range of 1 to 4.9 milliseconds. These currents decayed more slowly than the AMPA mediated synaptic currents, with an average time constant of 24 milliseconds and a range of 10 to 24 milliseconds. The mean amplitude of the currents at ±40 mV was 68 pA, with a range between 20 and 90 pA. Pharmacological studies were conducted on 9 of these 16 pairs of NT2N neurons. In all nine instances, application of bicuculline, a selective $GABA_A$ receptor antagonist, completely blocked the synaptic currents. These findings demonstrate that 29% of detected synapses between NT2N neurons were inhibitory and utilized GABA as their neurotransmitter.

DISCUSSION

These studies demonstrate that functional inhibitory and excitatory synapses form between cultured NT2N neurons when they are grown on astrocytes. Additionally, cultured primary astrocytes have profound effects on the morphological, electrophysiological and survival properties of the NT2N neurons. The punctate immunoreactive pattern seen with synapse-specific antibodies demonstrates that co-cultured NT2N neurons express synaptic proteins in appropriate patterns. EM studies document the existence of abundant spatially discrete membrane specializations characteristic of mature synapses. Vesicular morphologies, numbers and sizes are typical of primary neurons when the NT2N neurons are cultured on astrocytes, and scarce without co-culture. Electrophysiological studies provide evidence that the kinetics, ion selectivity, and pharmacology of NT2N synapses are qualitatively similar to those of efficacious neurons in primary culture only when co-cultured on astrocytes. Thus, the NT2N-astrocyte co-culture system is useful in studying neuronal glial interactions. Further, the ability of NT2N neurons to communicate through synaptic transmission comparable to that found between cultured primary neurons and to utilize more than one functional neurotransmitter phenotype as demonstrated herein is indicative of their therapeutic utility for selected neurodegenerative and post-traumatic disorders of the human nervous system.

Example 6

Human NT2N Neurons are Differentially Affected by Astrocytes Derived from Diverse CNS Regions:

The effects of primary rat astrocytes derived from diverse CNS regions on the maturation and morphology of pure NT2N neurons was examined. Maturation was assessed by the molecular markers adult tau and $P^{+++}NFH$. Morphology was assessed by cell size and shape.

Human NT2N neurons plated onto pure primary astrocyte monolayers prepared from rat cerebellum, cortex, hippocampus, striatum or spinal cord formed a monolayer network on top of the astrocytes. Astrocytes were identified by GFAP immunofluorescence. The NT2N neurons adopted a wide range of morphologies over time, including bipolar, tripolar and stellate shapes. This system allowed the NT2N neurons to be maintained in culture for longer than one year. By seven months in culture, NT2N neurons expressed the neuronal maturational markers adult tau and highly phosphorylated NFH. These markers are not expressed in vitro in the absence of astrocytes. The somal size distributions of the NT2N neurons were found to depend on the origin of the astrocyte base layers. On cerebellar, cortical or hippocampal astrocytes, NT2N neurons showed similar size distribution in a histogram, with a broad peak centered at 375–500 $\mu m^2$. On striatal astrocytes, NT2N neurons had a tightly clustered distribution at 250–374 $\mu m^2$, while NT2N neurons on spinal cord astrocytes showed a broad peak at 625–750 $\mu m^2$. NT2N neurons not located on GFAP immunoreactive cells remained in tight clusters with the same somal sizes as NT2N neurons at the time of plating, about 125 $\mu m^2$.

The following is a review of experiments performed to assess the effects of primary rat astrocytes derived from diverse CNS regions on NT2N neurons.

MATERIALS AND METHODS

Cortical, hippocampal, striatal, cerebellar, midbrain and brainstem astrocytes were cultured from P1 Sprague-Dawley rats, and spinal cord astrocytes were derived from E17 embryonic Sprague-Dawley rats. The tissue of interest was dissected out and the meninges were removed. All tissue was kept on ice in Dulbecco's modified Eagle's medium, high glucose (DMEM-HG; Gibco, Grand Island, N.Y.). The tissue was chopped into small pieces, and drawn through a 23 gauge needle with small amount of DMEM-HG (~200 $\mu l$). The resulting suspension was plated into 75 $cm^2$ Falcon flasks, and fed with DMEM-HG, 10% fetal bovine serum (FBS; Hyclone, Logan, Utah) 1% penicillin/streptomycin (P/S; Biosciences, Lenexa, Kans.) twice a week until confluence (1 to 2 weeks). When confluent, the flasks were treated with 50 $\mu M$ cytosine$\beta$-D-arabino-furanoside (ARAC, Sigma, St. Louis, Mo.) for 12 hours, after which the cells were chemically dissociated with EDTA and trypsin, heavily triturated, and plated 1:10 onto coverslips. These cultures were fed with DMEM-HG, 10% FBS, 1% P/S twice a week until confluence, after which they were fed every ten days with DMEM-HG, 10% FBS, 1% P/S and 1 $\mu M$ ARAC. At confluence, sister cultures were examined for astrocyte purity by GFAP immunoreactivity before NT2N neurons were plated onto the primary cultures.

Purified NT2N neuronal cells were prepared from the parent NT2 cells as described by Pleasure et al. 1992 *Journal of Neuroscience* 12(5):1802–15 and Kleppner et al. 1995 *Journal of Comparative Neurology* 357(4):618–32 with the following modifications. NT2 precursor cells were split 1:8 (~2.3×10⁶ cells) into 75 $cm^2$ flasks and fed twice weekly with DMEM-HG with 10% FBS, 1% P/S, and 10 $\mu M$ retinoic acid (RA) (Sigma, St. Louis, Mo.) for five weeks. Cells were then split 1:6 into two 225 $cm^2$ flasks and fed twice a week for ten days with DMEM-HG, 5% FBS, 1% P/S and mitotic inhibitors (1 $\mu M$ uridine, 1 $\mu M$ FUDR, and 0.1 $\mu M$ ARAC; Sigma, St Louis, Mo.). At this point, a pure population of NT2N neuronal cells was dislodged from the flasks and plated onto pure, confluent astrocyte monolayers.

Immunohistochemistry:

For detection of neuronal and astrocytic markers, cells were washed with PBS (pH 7.3) and fixed with 4% paraformaldehyde for ten minutes at room temperature. The coverslips were overlaid with primary antibodies in PBS with 2% Triton X-100 overnight at 4° C. The coverslips were washed three time with PBS over one hour; overlaid with Texas Red (TXR) and fluorescein isothiocyanate (FITC)-coupled secondary antibodies (Jackson Immunoresearch, West grove, Pa.) for one hour at room temperature; washed three times in PBS over one hour, and mounted with an anti-fade mounting agent (Fluoromount-G, Southern Biotechnology Associates, Inc., Birmingham, Ala.). The primary antibodies used were against neurofilament M (anti-human specific NFM), HO14, synapsin I (Molecular Probes, Eugene, Oreg.), MAP2 (AP14), GFAP (2.2B10), glutamate decarboxylase (GAD-1), highly phosphorylated neurofilament H (RMO217 and RMO24) and adult tau isoform (189 and 304).

Image Analysis And Quantification:

Images were captured by video camera signal integration and analyzed using Northern Exposure software. NT2N neuronal shapes and sizes were measured from seven month old co-cultures of NT2N neurons on cerebellar, cortical, hippocampal, striatal and spinal astrocytes. Three coverslips, immunostained with either GAD-1 and 2.2B10 or AP14 and HO14, were analyzed for each co-culture condition. Twenty fields were captured at 10× from each coverslip and all clearly visible NT2N neurons were analyzed. Using Northern Exposure software, neurons outlined by hand were measured and cells shapes were graded.

RESULTS

NT2N Neurons Mature in Vitro When Co-cultured with Primary Astrocytes:

NT2N neurons cultured on astrocytes expressed the maturational marker, $P^{+++}NFH$ as early as two months in vitro. By seven months, NT2N neurons showed abundant expression of $P^{+++}NFH$ and adult tau. Pure NT2N neurons do not survive for more than three months in vitro and never acquire either of these adult maturational markers.

CNS Origin of Primary Astrocytes Affects NT2N Neuronal Morphologies

As discussed previously, pure NT2N neurons maintain small, spherical morphologies and migrate into tight clusters of neurons, while NT2N neurons located on astrocytes disperse to form a monolayer network of cells with a variety of morphologies. It was found that when NT2N neurons were located on non-astrocyte primary cells, they still survived for long times in culture, but they either migrated into dense clusters or adopted large, irregular morphologies. Additionally, when cultured on astrocytes derived from different CNS regions, the distribution of NT2N neuronal morphologies changed.

Slight differences in NT2N morphologies cultured with astrocytes from different CNS areas were visible after one month of co-culture, and progressed with time in culture. By two months of co-culture, NT2N neurons on striatal astrocytes were smaller and rounder than those on cortical astrocytes, while those plated on spinal cord astrocytes exhibited a corresponding mix of large and small sizes. NT2N neurons on hippocampal or cerebellar astrocytes showed similar size distributions to those cultured on cortical astrocytes.

Striking differences were seen in cell size by seven months of co-culture. At this time, NT2N neurons had distinct somal morphologies, including bipolar, tripolar and stellate morphologies. Again, the most obvious differences in neuronal morphology were found in the smaller, rounder cells located on striatal astrocytes, and larger neurons on spinal cord astrocytes. The morphologies of NT2N neurons on cerebellar astrocytes were similar to those on cortical or hippocampal astrocytes.

Somal morphology was assessed by grouping NT2N neurons as: round, monopolar, bipolar, tripolar, trapezoidal, stellate irregular, fibrous, or not clearly identifiable. Round, bipolar and tripolar cells were the most populous subsets. No obvious astrocyte related differences in somal morphology distributions were seen within the other classification of cell types. Seventy-one percent of all NT2N neurons on striatal astrocytes had round, bipolar or tripolar morphologies, whereas only 50% of all NT2N neurons located on the other CNS astrocytes developed these morphologies. Further, fewer tripolar cells, 6% compared with the approximately 20% found on other astrocytes, were observed.

Quantification of these results showed clear differences in the somal size distribution of NT2N neurons on primary astrocytes derived from different CNS areas. Sizes were plotted in 125 $\mu m^2$ bins on a histogram as the fraction of the total number of cells measured for each area. Although morphologically similar NT2N neurons can be found on top of astrocytes cultured from any CNS region, the overall distribution of morphologies changed with each CNS region. This is reflected by the differences in the shapes of the distribution curves, while their total ranges overlap. The size distribution of NT2N neurons on cortical, cerebellar or hippocampal astrocytes had broad peaks centered about 375–500 $\mu m^2$, while the distributions on striatal astrocytes (n=427) had a narrow size peak, centered at 250–375 $\mu m^2$. NT2N neurons on spinal cord astrocytes (n=254) had the broadest size distribution, centered at 625–750 $\mu m^2$. NT2N neurons which remained in tight clusters (not located on GFAP immunoreactive cells) had size distributions similar to, but slightly smaller than, the size distribution of NT2N neurons located on striatal astrocytes.

DISCUSSION

These experiments demonstrate that post-mitotic NT2N neurons can acquire phenotypic differences, as they differentially respond to astrocytes cultured from different CNS regions. Further, the mix of NT2N neuronal sizes found on mixed striatal and spinal cord astrocytes indicates that astrocyte effects on neuronal morphology are contact mediated. These experiments also demonstrate the ability of NT2N neurons to express the adult maturational markers $P^{+++}NFM$ and adult tau when co-cultured on primary astrocytes. These experiments thus define a useful system to study neuron/glia interactions and phenotypic commitment of post-mitotic human neurons. Further, these experiments demonstrate that neuronal cells with a selected phenotype can be obtained by co-culturing neuronal cells with astrocytes from a region of the of the central nervous systems exhibiting the selected phenotype.

Example 7

Graft Neurons Restore Function in a Spinal Cord Injury Model:

The capacity of grafted neurons to promote axonal regeneration and functional recovery in vivo was investigated using an animal model of spinal cord injury. Transplants of NT2N cells into the hemisected cervical spinal cords of adult rats were evaluated. Functional recovery and axonal regeneration after transplantation of NT2N neurons in the hemisected cervical cord rodent model of spinal cord injury was observed.

The following is a review of experiments demonstrating functional recovery in a rodent model spinal cord injury in rats with NT2N implants.

MATERIALS AND METHODS

Twenty one female Wistar rats (225–250g) were first trained in the "staircase test" to assess forepaw function prior to receiving a C3–C4 laminectomy and cervical cord hemisection, which caused loss of function in one upper limb. Immediately following hemisection, animals (7 per group) received: 1) cell suspensions of NT2N neurons above, below and within the transection site (double grafts);

2) transplants within the transection site only (bridge grafts); or 3) no transplants for transection control. Animals in the double graft group received transplants of 250,000 NT2N cells into the cord at sites distal and proximal to the lesion and $10^6$ NT2N Neurons into the lesion, and animals with bridge grafts received $10^6$ cells.

Skilled forelimb function was assessed using a staircase apparatus consisting of a plastic box with built-in left and right staircases with five steps each. The staircases were separated from each other in such a manner that it was impossible for an animal to reach the right staircase with any limb other than the right forelimb and vice versa. The five steps on each staircase were loaded with small food pellets, and the animals were allowed to acquire as many food pellets as possible using each forelimb independently in a 15 minute period. The number of pellets consumed by the rat were counted at the end of each test period and recorded as "number of pellets taken". Each animal was assessed in the staircase test preoperatively and at 1-, 4- and 8 weeks post-implant. At 8-weeks post-implant, animals were sacrificed and sections of the spinal cord were processed for serotonin (5-HT) immunohistochemistry to identify descending serotonergic fibers.

Improvement In Forelimb Function Observed:

In animals receiving double grafts, improvement in forelimb function was observed at eight weeks following transplant in the staircase test, and 5-HT positive fibers could be seen growing through the hemisected site and innervating the distal spinal cord. In animals receiving a bridge graft, limited improvement in forelimb function was observed and 5-HT positive fibers could be seen penetrating the hemisected site for a short distance but not innervating the distal spinal cord. In control animals with hemisection only, forelimb function decreased slightly, and no fibers could be seen penetrating the lesion to the distal spinal cord.

Example 8

Human Surgery:

In this example, removal of a cyst is described. However, these procedures are also clearly applicable to other types of damage to the spinal cord.

Prior to transplant, it is preferable to diagnose location and presence of any cysts and their volume by MRI and CT.

Neuronal cells for implant are processed as discussed above. An appropriate volume of cells (at least $10^6$ cells) equal to that of the cyst to be removed is optionally added to a volume of MATRIGEL (or other gel intended for parenteral use).

The surgeon locates the appropriate level(s) of the spine and accesses the spinal canal to remove the cyst and other debris which might block nerve regeneration, using known techniques. Next the surgeon places aliquots of at least $5\times10^5$ cells against the caudal and rostral ends of the exposed spinal cord. Aliquots with more cells may be used depending upon the size of the damaged area and the patient. The wound receives the cells embedded in MATRIGEL and is packed with sterile resorbable material. Next the layers surrounding the spinal cord are closed, as are the more superficial layers. Beginning at surgery, methylprednisolone is administered in the usual spinal injury dose and is continued for as long as the surgeon considers necessary, which may vary from 1 week to several months. In circumstances in which the cells are histocompatible with the recipient, or other situations under the physician's determination, anti-rejection therapy may not be needed.

What is claimed is:

1. A method of integrating post-mitotic human NT2N neurons into the spinal cord of a mammal comprising implanting a sample of at least 95% pure, stable, homogeneous post-mitotic human NT2N neurons into the spinal cord of said mammal, wherein said post-mitotic human NT2N neurons integrate into the spinal cord of said mammal.

2. The method of claim 1 wherein said post-mitotic human NT2N neurons are implanted at or near a site of injury in the spinal cord of said mammal.

3. The method of claim 1 wherein said post-mitotic human NT2N neurons are implanted at multiple sites in the mammal's spinal cord.

4. A method of treating spinal cord injury in a mammal comprising implanting a sample of at least 95% pure, stable, homogeneous post-mitotic human NT2N neurons into the spinal cord of the mammal, wherein said post-mitotic human NT2N neurons integrate into the spinal cord and wherein the implantation of said post-mitotic human NT2N neurons promotes axonal regeneration and ameliorates the spinal cord injury.

5. A method of increasing levels of expression of tyrosine hydroxylase in the central nervous system of a mammal comprising implanting a sample of at least 95% pure, stable, homogeneous post-mitotic human NT2N neurons into the spinal cord of said mammal, wherein said post-mitotic human NT2N neurons integrate into the spinal cord and increase the level of tyrosine hydroxylase in the central nervous system of said mammal.

6. A method of producing modified post-mitotic human NT2N neurons comprising co-culturing said post-mitotic human NT2N neurons with astrocytes isolated from a region of the central nervous system of a mammal, wherein said post-mitotic human NT2N neurons are modified to express maturational marker, $P^{+++}NFH$.

* * * * *

UNITED STATES PATENT AND TRADEMARK OFFICE
CERTIFICATE OF CORRECTION

PATENT NO.   : 6,214,334 B1
DATED        : April 10, 2001
INVENTOR(S)  : Lee and Trojanowski It is certified that error appears in the above-identified patent and that said Letters Patent is hereby corrected as shown below:

Column 4,
Line 12, please delete "region of the of the" and insert -- region of the --.

Column 17,
Line 8, example 1, please delete "($\beta_2$" and insert -- $\beta_2$ --.

Column 19,
Line 22, table 2, please delete "pg/ml" and insert -- $\mu$g/ml --.

Column 33,
Line 19, example 5, please delete "± 40" and insert -- +40 --.

Signed and Sealed this

Eleventh Day of March, 2003

JAMES E. ROGAN
*Director of the United States Patent and Trademark Office*